US008392029B2

(12) United States Patent
Nakamoto et al.

(10) Patent No.: US 8,392,029 B2
(45) Date of Patent: Mar. 5, 2013

(54) ODOR BLENDER, ODOR RECORDER, ODOR REPRODUCER, AND ODOR RECORDING AND REPRODUCING SYSTEM

(75) Inventors: Takamichi Nakamoto, Tokyo (JP); Hai Dinh Minh Pham, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 1121 days.

(21) Appl. No.: 12/296,930

(22) PCT Filed: Mar. 6, 2007

(86) PCT No.: PCT/JP2007/054293
§ 371 (c)(1),
(2), (4) Date: Oct. 10, 2008

(87) PCT Pub. No.: WO2007/122879
PCT Pub. Date: Nov. 1, 2007

(65) Prior Publication Data
US 2009/0133764 A1     May 28, 2009

(30) Foreign Application Priority Data
Apr. 11, 2006    (JP) ................................. 2006-108205

(51) Int. Cl.
*G05D 11/02* (2006.01)
(52) U.S. Cl. ...................................... 700/285; 700/283
(58) Field of Classification Search .................. 700/282, 700/283, 285
See application file for complete search history.

(56) References Cited

U.S. PATENT DOCUMENTS 5,177,994 A * 1/1993 Moriizumi et al. .......... 73/23.34
5,724,256 A     3/1998 Lee et al.

FOREIGN PATENT DOCUMENTS

| JP | 63-187153 A | 8/1988 |
|---|---|---|
| JP | 2000-156647 A | 6/2000 |
| JP | 3331371 B2 | 7/2002 |
| JP | 2003-279459 A | 10/2003 |
| JP | 3722000 B2 | 9/2005 |

OTHER PUBLICATIONS

Yamanaka et al., "Study of odor blender using solenoid valves controlled by delta-sigma modulation method for odor recorder", Elsevier Science 2002.*
International Search Report dated May 1, 2007 including English translation (Five (5) pages).

* cited by examiner

*Primary Examiner* — Mohammad Ali
*Assistant Examiner* — Carlos Ortiz Rodriguez
(74) *Attorney, Agent, or Firm* — Crowell & Moring LLP

(57) ABSTRACT

An odor blender is provided in which a number of component odor gases may be increased without increasing the number of carrier gas containers while ensuring a single odor gas concentration is not reduced. The odor blender includes N odor containers, M less than N) carrier gas containers, a blend line leading to a blend part for blending the odor gases, a bypass line for discharging odor gases, and solenoid valves for switching the containers between the blend line and the bypass line. A computer sets the number of odor containers connected to the blend line at the same time to M or less, connects the same number of carrier gas containers to the bypass line as the number of odor containers connected to the blend line, and controls timing of connection of odor containers to the blend line based on a predetermined mixing ratio of the component odor gases.

13 Claims, 16 Drawing Sheets

FIG.8
(a)
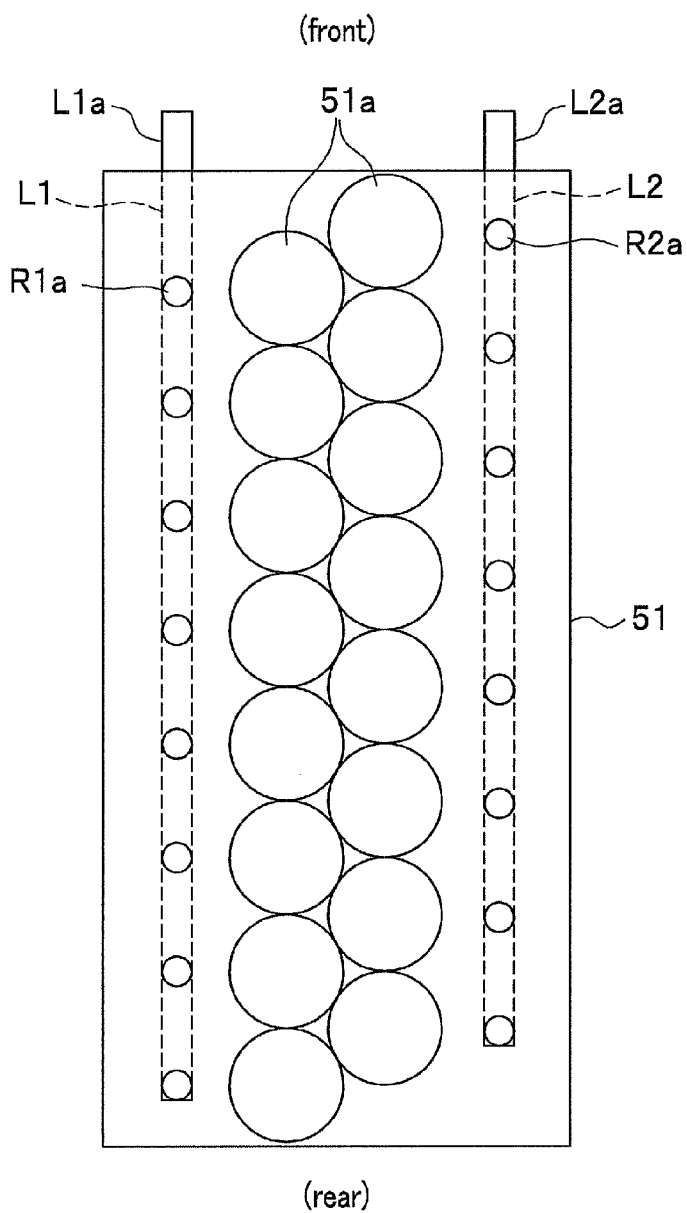
(b)
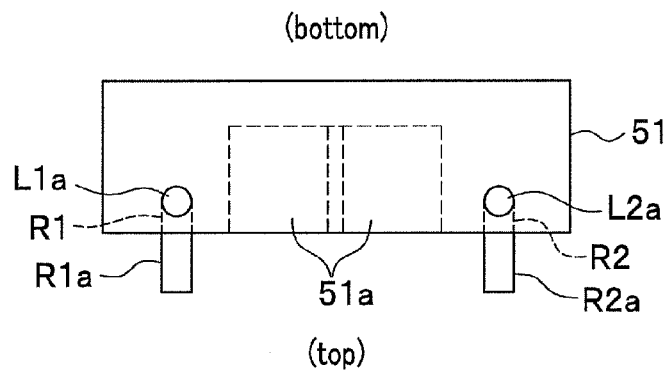

FIG.9
(a)
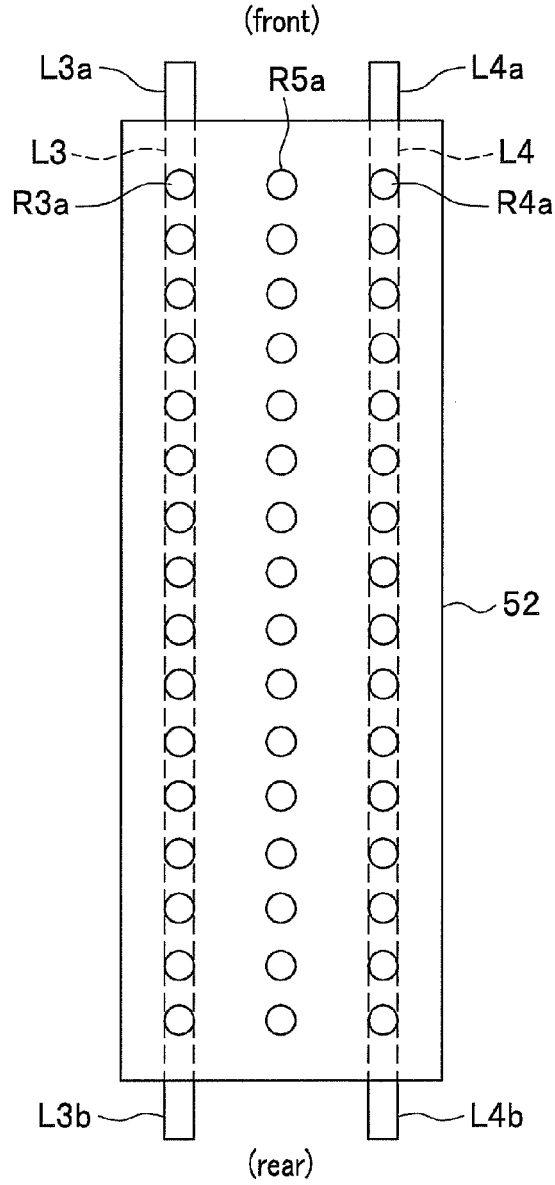
(b)
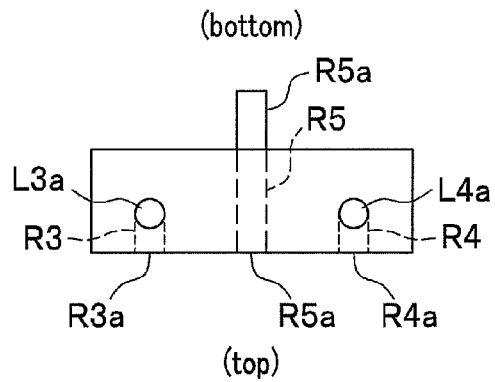

FIG.13
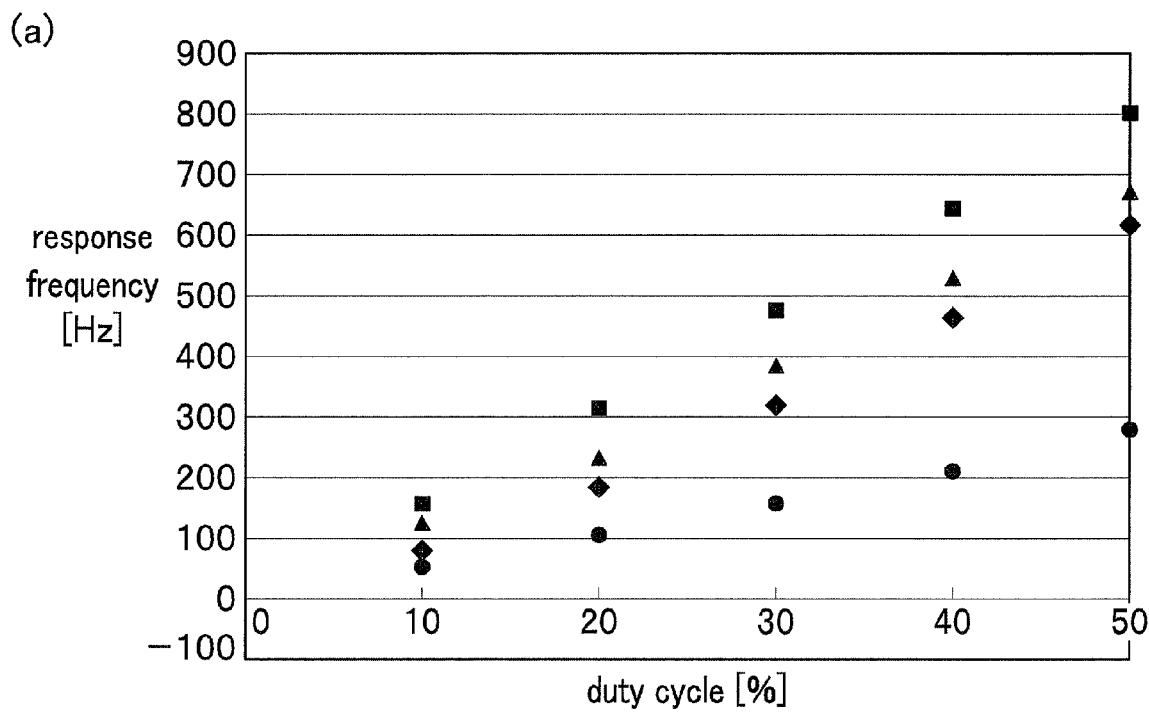
(a)
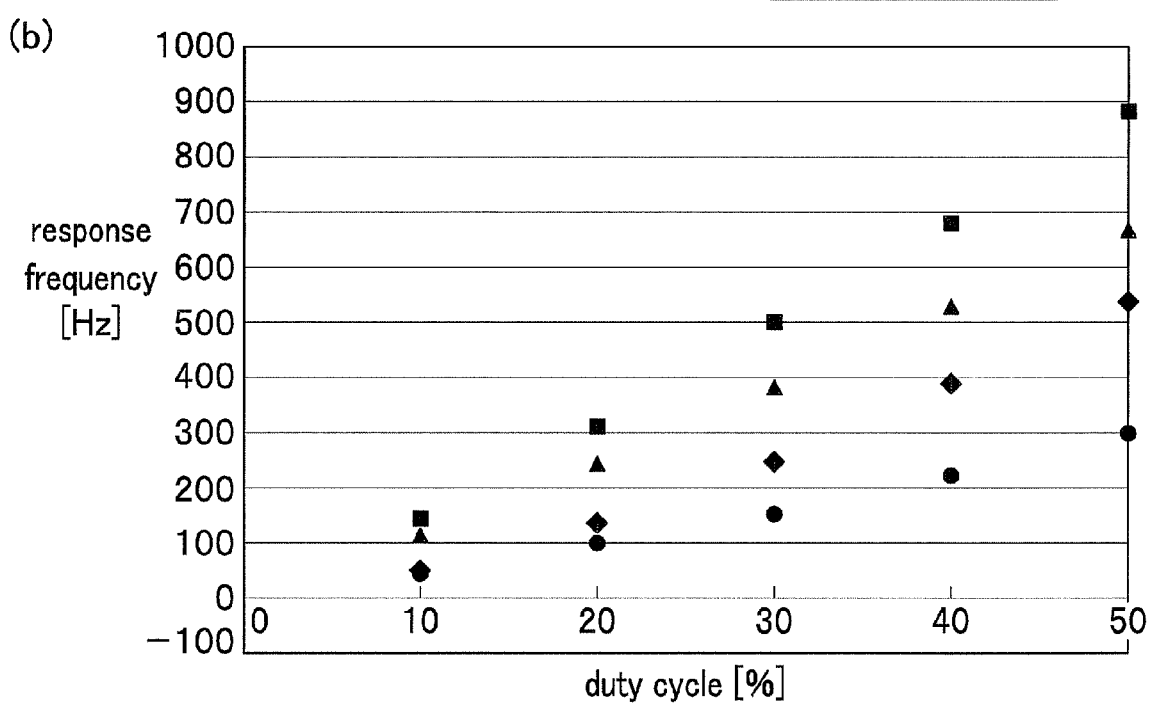
(b)

FIG.14
(a)
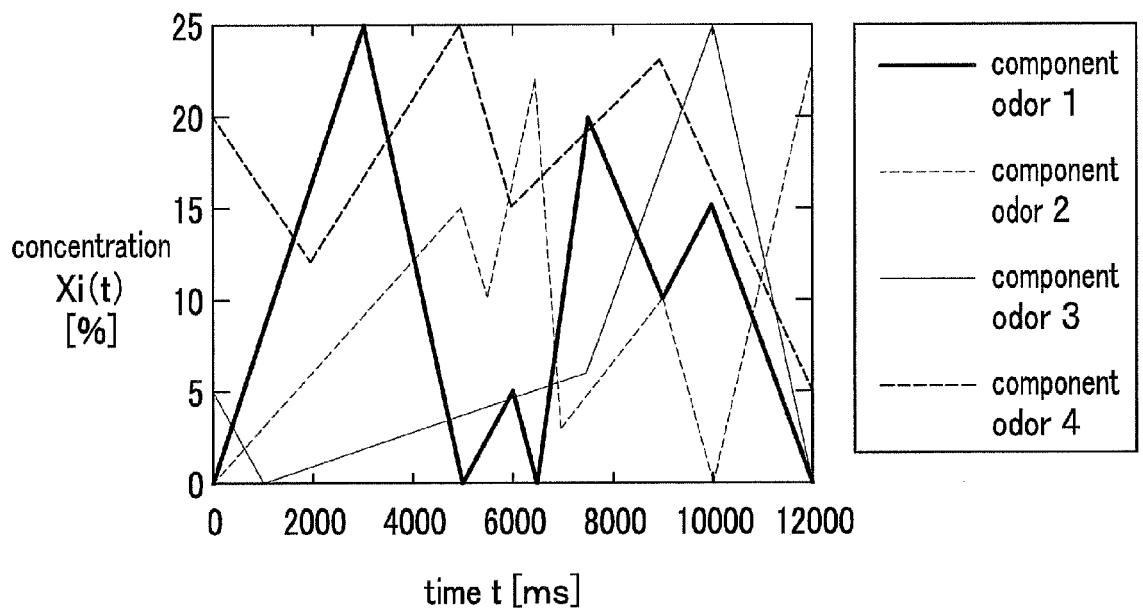
(b)
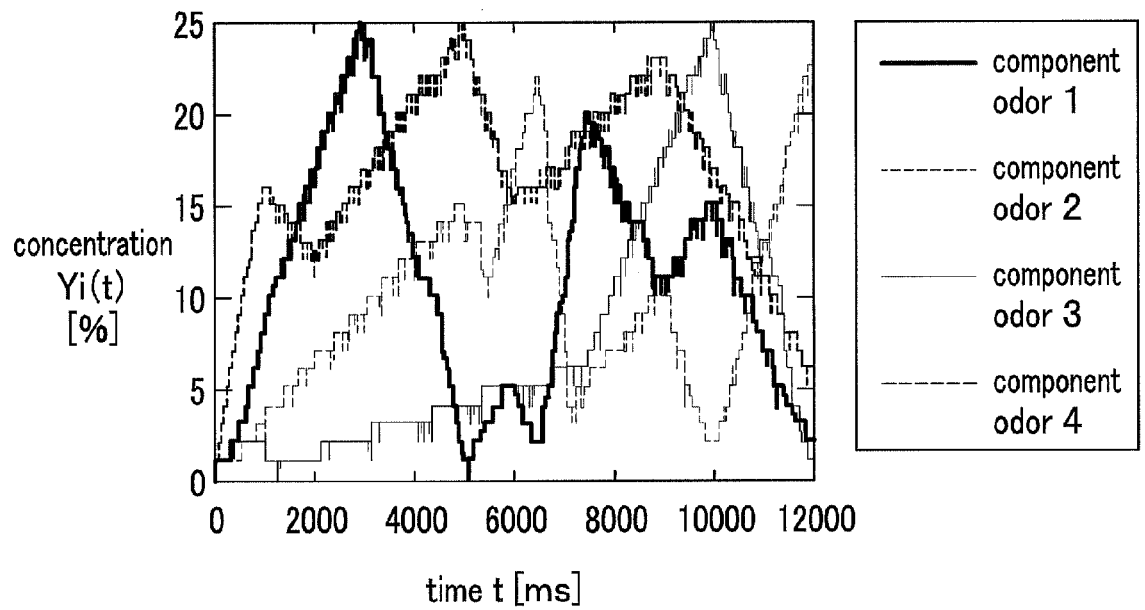

ODOR BLENDER, ODOR RECORDER, ODOR REPRODUCER, AND ODOR RECORDING AND REPRODUCING SYSTEM

TECHNICAL FIELD

The present invention relates to an odor blender for blending an odor by mixing component odor gases, an odor recorder, an odor reproducer and an odor recording and reproducing system.

BACKGROUND ART

Conventionally, as an apparatus for blending an odor by mixing multiple component odor gases, there can be mentioned an apparatus in which predetermined amounts of component odor gases are supplied from respective supply sources through respective mass flow controllers, and a blend is made (Patent Document 1). In this apparatus, expensive mass flow controllers are required as many as the number of the types of component odor gas, and thus there is a problem that the entire cost becomes high as the number of types of component odor gas increases.

Accordingly, the present inventors proposed an apparatus in which inexpensive 3-way solenoid valves are used instead of mass flow controllers, an opening and closing frequency of the solenoid valve is controlled by $\Delta\Sigma$ modulation method, and the component odor gases with desired concentrations are supplied, for blending an odor (Patent Document 2). With respect to this apparatus, descriptions will be made with reference to FIGS. 15 and 16. Herein, FIG. 15 is a diagram showing a structure of an odor blender described in Patent Document 2, and FIG. 16 is a diagram illustrating modes of opening and closing of the 3-way solenoid valve by $\Delta\Sigma$ modulation.

The apparatus shown in FIG. 15 is an odor blender in which an odor of an odor gas of interest (target odor gas) is measured, and a mixing ratio (recipe) of two component odor gases is determined for reproducing the odor of the target odor gas. As shown in FIG. 15, the apparatus includes: carrier gas containers 1017 and 1021; a sample container 1018 for the target odor gas; component odor gas containers 1019 and 1020; a solenoid valve 1027; 3-way solenoid valves 1028a, 1028b, 1029a and 1029b; a sensor cell 1030; valved flowmeters 1040 and 1041; a suction pump 1031; a frequency counter 1032; and a computer 1033.

In this apparatus, the sensor cell 1030 has multiple QCM (Quartz Crystal Microbalance) sensors 1030A, 1030B . . . . Outputs of the QCM sensors are measured by the frequency counter 1032, and the measured values (sensor output vectors) are transmitted to the computer 1033. With these sensor outputs, the odor can be quantitatively determined.

A measurement system of this apparatus is a gas flow measurement system, and either the carrier gas (air, dry air or the like) or the target odor gas is supplied to the sensor cell 1030 at a constant flow rate. The gas flow is driven by the suction pump 1031 through the valved flowmeter 1040.

First, a target odor gas with which an odor is to be recorded is charged in the sample container 1018, and by opening the solenoid valve 1027, the target odor gas is supplied to the sensor cell 1030, where the odor is measured. The measured value (sensor output vector) is stored in the computer 1033. After the completion of the measurement, the solenoid valve 1027 is closed and the supply of the target odor gas is stopped. The opening and closing for each of the solenoid valve 1027 and the 3-way solenoid valves 1028a, 1028b, 1029a and 1029b is controlled by the computer 1033.

Next, by controlling the frequency of the opening and closing of the 3-way solenoid valves 1028a and 1028b, component odor gases with predetermined concentrations are supplied from the component odor gas containers 1019 and 1020 to the sensor cell 1030 to thereby blend an odor. The sensor output vectors of the blended odor are measured using the QCM sensors 1030A, 1030B . . . as well as the frequency counter 1032, and the computer 1033 compares the measured vectors with the sensor output vectors of the target odor. Based on a result of this comparison, the computer 1033 calculates a concentration of each component odor gas to be supplied, and in accordance with the calculated concentration, alters the frequency of the opening and closing of the 3-way solenoid valves 1028a and 1028b.

FIG. 16 shows modes of the opening and closing of the 3-way solenoid valves 1028a and 1028b by $\Delta\Sigma$ modulation. As shown in A and B in the drawing, the opening and closing of the 3-way solenoid valves 1028a and 1028b is controlled in every short time period, such as about several ms to 100 ms. The time period indicated as a shaded area means a time period in which the corresponding component odor gas is supplied to the sensor cell 1030, and there are three modes including: a mode in which the component odor gases A and B are supplied to the sensor cell 1030 at the same time; a mode in which only one of the component odor gas is supplied, and a mode in which neither of them is supplied. Therefore, supply amount may change depending on the opening and closing state of the solenoid valves 1028a and 1028b. In addition, since the control is made in every short time period, it is difficult to accurately synchronize the solenoid valves 1028a and 1028b.

In order to stably generate a blended odor regardless of the connection mode of the component odor gas containers 1019 and 1020 with the sensor cell 1030, the flow rate of the gas supply to the sensor cell 1030 should be constant. Accordingly, relative to the component odor gas containers 1019 and 1020, the corresponding carrier gas containers 1017 and 1021 are provided, and by controlling the 3-way solenoid valves 1028a and 1029a (1028b and 1029b) as a pair, a structure is made in which either the component odor gas or the carrier gas is supplied at the same flow rate to the sensor cell 1030, from each pair of the component odor gas container and carrier gas container. Further, in order to retain the gas concentration of the component odor in each headspace of the component odor gas containers 1019 and 1020 constant, the 3-way solenoid valves are used as a solenoid valve, and when the 3-way solenoid valves 1028a and 1028b are in a closed mode (in which the component odor gas is not supplied to the sensor cell 1030), the containers are connected to a gas flow line driven by the suction pump 1031 through the valved flowmeter 1041 (hereinafter, referred to as "bypass line"), to thereby retain the flow rates in the component odor gas containers 1019 and 1020 constant. With respect to the carrier gas containers each of which makes a pair with the corresponding component odor gas container, a symmetrical configuration similar to that of the component odor gas containers is made, and from each pair of the component odor gas container and the carrier gas container, the component odor gas and the carrier gas are supplied to the sensor cell 1030 and the bypass line in a complementary manner.

(Patent Document 1)

Japanese patent publication No. 3331371A (paragraph 0019 and FIG. 1)

(Patent Document 2)
Japanese patent publication No. 3722000 (paragraphs 0021 to 0027 and FIG. 2)

DISCLOSURE OF THE INVENTION

Problem to be Solved by the Invention

With respect to the odor blender disclosed in Patent Document 2, in order to increase the number of the types of component odor gas to be used in blending, the number of the component odor gas containers, together with the same number of the carrier gas containers, should be increased, leading to a problem of a large apparatus in size. In addition, even when the component odor gas is not supplied from each component odor gas container, the carrier gas of the same flow rate is supplied to the sensor cell 1030, and thus, if N component odor gas containers are used, a concentration of a single component odor gas supplied is limited (diluted) to 1/N of the gas concentration in the headspace of the component odor gas container, at most. Accordingly, as the number of the types of component odor gas to be used is increased, the maximum concentration to be supplied becomes low, and thus there arises a problem that an odor with sufficient intensity cannot be provided and a range of reproducible odor becomes narrow.

Therefore, it is an object of the present invention to provide an odor blender in which there is no need to increase the number of the carrier gas containers, and at the same time, the maximum gas concentration supplied from a single component odor gas is not reduced, even when the number of the types of component odor gas is increased. It is another object of the present invention to provide an odor recorder, an odor reproducer, an odor recording and reproducing system using such an odor blender.

Means to Solve the Problem

Accordingly, in order to attain the above-mentioned object, there is provided an odor blender as set forth in Claim 1 including N (wherein N is an integer of 2 or more) component odor containers each configured to supply a component odor gas, M (wherein M is an integer of 1 or more and less than N) carrier gas containers each configured to supply a carrier gas, a blend part configured to blend the component odor gases, a blend line configured to lead the component odor gases from the N component odor containers to the blend part, a bypass line configured to discharge the component odor gases from the N component odor containers, (N+M) solenoid valves each configured to switch a connection from the N component odor containers and the M carrier gas containers, to between the blend line and the bypass line, and a control unit configured to control the switching of the connections by the (N+M) solenoid valves, wherein the control unit sets the number of the component odor containers connected to the blend line at the same time to M or less out of the N component odor containers; connects the same number of the carrier gas containers to the bypass line as the number of the component odor containers connected to the blend line; and controls a time frame for the connection from the component odor container to the blend line per predetermined time period, based on a predetermined mixing ratio of the N component odor gases.

According to this structure of the odor blender, out of the N component odor containers containing the component odor gas, the number of the component odor containers connected to the blend line at the same time is set to M or less (wherein M is the number of the carrier gas containers), and in addition, the switching of the connections by the solenoid valves is controlled in such a manner that the same number of the carrier gas containers is connected to the bypass line as the number of the component odor containers connected to the blend line. As a result, the total number of the connected component odor containers and connected carrier gas containers becomes constant for each of the blend line and the bypass line, and therefore the flow rate of the flow current in each of the blend line and the bypass line becomes constant. Consequently, regardless of the connection modes from the component odor container to the blend line and bypass line, the flow rate of the flow current in each component odor container always becomes constant, and accordingly, simply by controlling the time frame for connecting each component odor container to the blend line per unit time using the solenoid valve corresponding to each component odor container, the component odor gas in a stable amount can be supplied to the blend part.

An odor blender as set forth in Claim 2 is the odor blender according to Claim 1, wherein the component odor gas is supplied from a headspace of the corresponding component odor container.

According to this structure of the odor blender, due to the structure of the odor blender as set forth in Claim 1, regardless of the connection modes of the component odor container with the blend line or the bypass line, the flow rate of the flow current in each component odor container always becomes constant, and therefore the gas concentration in the headspace of each component odor container is always retained constant, and the component odor gas with a stable gas concentration can be supplied to the blend part.

An odor blender as set forth in Claim 3 is the odor blender according to Claim 1 or 2, wherein each of the blend line and the bypass line has a flow regulating unit configured to adjust a corresponding flow rate.

According to this structure of the odor blender, the flow rate of each of the blend line and the bypass line is adjusted to a predetermined value by the flow regulating unit, such as valved flowmeter, and therefore, in accordance with the opening and closing time period of the solenoid valve, a predetermined amount of the component odor gas can be supplied from each component odor container.

An odor recorder as set forth in Claim 4 includes the odor blender according to any one of Claims 1 to 3, and a measuring unit configured to measure odor disposed on the blend line, wherein the control unit determines the mixing ratio of component odor gases base on a target value determined in advance and a measured value of an odor blended in the blend part measured by the measuring unit.

According to this structure of the odor recorder, the measured value or the like of the target odor gas, which was obtained separately, is set as a target value, and a component odor gas is blended by the odor blender. The mixing ratio of the component odor gases is adjusted in such a manner that the measured value of the blended odor measured by the measuring unit approaches the target value, and the adjustment of the mixing ratio and measurement of the blended odor are repeated until the target value and the measured value of the blended odor becomes equal, at which the mixing ratio is determined.

An odor reproducer as set forth in Claim 5 includes the odor blender according to any one of Claims 1 to 3, wherein a gas flow of each of the blend line and the bypass line is driven by a gas flow driving unit disposed on an upstream end of the gas flow.

According to this structure of the odor reproducer, a carrier gas pressurized by the compressor or the like is supplied from an upstream side of the gas flow line to drive the gas flow, and the odor blended in the blend line is dispersed.

An odor recording and reproducing system as set forth in Claim 6 includes: at least one odor recorder according to Claim 4 which is connected to a network, at least one odor reproducer according to Claim 5 which is connected to the network, and a management computer which is connected to the network, wherein the management computer obtains through the network the mixing ratio determined by the odor recorder, and the management computer sends the obtained mixing ratio to the odor reproducer through the network and controls the odor reproducer to blend the component odor gas based on the obtained mixing ratio.

According to this structure of the odor recording and reproducing system, the management computer manages the recipe (mixing ratio of the component odor gases) obtained from the odor recorder through the network and controls the odor reproducer at a remote location to disperse the odor based on the recipe.

An odor blender as set forth in Claim 7 includes N (wherein N is an integer of 2 or more) component odor containers each configured to supply a component odor gas, M (wherein M is an integer of 1 or more and less than N) carrier gas containers each configured to supply a carrier gas, a blend part configured to blend the component odor gases, a blend line configured to lead the component odor gases from the N component odor containers to the blend part, a bypass line configured to discharge the component odor gases from the N component odor containers, (N+M) solenoid valves each configured to switch a connection from the N component odor containers and the M carrier gas containers, to between the blend line and the bypass line, and a control unit configured to control the switching of the connections by the (N+M) solenoid valves, wherein, when $x_i(t)$ represents a preset concentration of a component odor i at the present moment t, and $y_i(t)$ represents an average concentration for past time periods $n\tau$, the control unit selects, every predetermined unit time $\tau$, a single component odor container that supplies a component odor gas with which $x_i(t)$ becomes larger than $y_i(t-1)$ and a relative error of both becomes the maximum, and connects the selected component odor container to the blend line.

According to this structure, by selecting per unit time, as a component odor container to be connected to the blend line, a component odor container which supplies the component odor whose concentration has the largest difference from the concentration of the component odor of the component odor container connected at the present moment, a homogeneous odor blending can be attained with a high time resolution.

An odor blender as set forth in Claim 8 is the odor blender according to Claim 7, wherein, when $x_i(t)$ represents the preset concentration of the component odor i at the present moment t, and $y_i(t)$ represents a ratio of the connection of the component odor i to the blend line during past time periods $n\tau$ (wherein n is a positive integer) from the moment t, the control unit selects, every predetermined unit time $\tau$, a single component odor container that supplies a component odor gas with which $x_i(t)$ becomes larger than $y_i(t-1)$ and the relative error $(x_i(t)-y_i(t-1))/x_i(t)$ becomes the maximum, and connects the selected component odor container to the blend line.

According to this structure, by selecting per unit time, as a component odor container to be connected to the blend line, a component odor container which supplies a component odor that makes the relative error maximum based on the component odor of the component odor container connected at the present moment, a homogeneous odor blending can be attained with a high time resolution.

An odor blender as set forth in Claim 9 is the odor blender according to Claim 7 or 8, wherein, when there is no corresponding component odor, solely a carrier gas container is connected to the blend line at the moment t.

According to this structure, $x_i(t)$ also changes dynamically, and there are cases where $y_i(t)$ becomes larger than $x_i(t)$ when $x_i(t)$ is smaller as compared with $x_i(t)$ at a previous moment. Therefore, when the average concentration $y_i(t)$ is larger than the preset concentration $x_i(t)$, the value of $y_i(t)$ becomes smaller and closer to $x_i(t)$.

Effect of the Invention

According to the invention as set forth in Claim 1, since the number of the carrier gas containers can be reduced to M, which is smaller than the number of the component odor containers (N), the types of the component odor gas can be increased simply by increasing a single component odor container per one type of component odor gas. In addition, since the number of the component odor containers connected to the blend line at the same time is set to M, even when the number of the types of component odor gas is increased, a maximum gas concentration supplied from a single component odor gas is not reduced in the odor blender.

According to the invention as set forth in Claim 2, from the headspace of each component odor container, the component odor gas with a constant gas concentration can be supplied for blending an odor. Therefore, fluctuations of component amounts in the component odor gas in a blended odor can be suppressed small.

According to the invention as set forth in Claim 3, the flow rate of the flow current in the blend line and the bypass line can be adjusted to a predetermined value, and therefore, the odor can be blended with an excellent reproducibility.

According to the invention as set forth in Claim 4, even when the number of the types of component odor gas is increased, it is not necessary to increase the number of the carrier gas containers, and thus an apparatus can be retained compact and a blend odor can be blended with a wide reproducibility, and therefore, the target odor can be recorded with high accuracy.

According to the invention as set forth in Claim 5, since the gas flow driving unit is disposed on the upstream side of the gas flow line to disperse the blended odor, the odor can be reproduced without deteriorating the blended odor.

According to the invention as set forth in Claim 6, since the system is formed of compact odor recorder and odor reproducer, collection of odor and reproduction of odor can be performed in a wide range, without locational constraints.

According to the invention as set forth in Claims 7 and 8, by selecting per unit time, as a component odor container to be connected to the blend line, a component odor container which supplies the component odor whose concentration has the largest difference from the concentration of the component odor of the component odor container connected at the present moment, a homogeneous odor blending can be attained with a high time resolution. With this odor blender, by supplying the odor to the odor sensor having a high time resolution, such as about ⅛ second or ¹⁄₁₆ second order, while dynamically changing the odor, a transient response of the odor sensor can be accurately measured. In addition, the process of actually diffusing the odor in the atmosphere can be more accurately regenerated.

According to the invention as set forth in Claim 9, when the average concentration yi(t) is larger than the preset concentration xi(t), the value of yi(t) becomes smaller and closer to xi(t).

BRIEF DESCRIPTION OF DRAWINGS

FIG. 8 shows a lower manifold of the odor blender shown in FIG. 7, in which (a) is a plan view seen from above, and (b) is a side view seen from the front.

FIG. 9 shows an upper manifold of the odor blender shown in FIG. 7, in which (a) is a plan view seen from above, and (b) is a side view seen from the front.

FIG. 13 shows graphs indicating relationships between concentration of component odor gas supplied by an odor blender according to one embodiment and a sensor output, in which (a) is measurement results when a component odor gas is supplied from a component No. 2, and (b) is measurement results when a component odor gas is supplied from a component No. 32.

FIG. 14(a) is a graph showing a profile of a preset concentration in an experiment 2, and (b) is a graph showing a profile of concentration of odor blended by an odor blender in the experiment 2.

Figure 1:
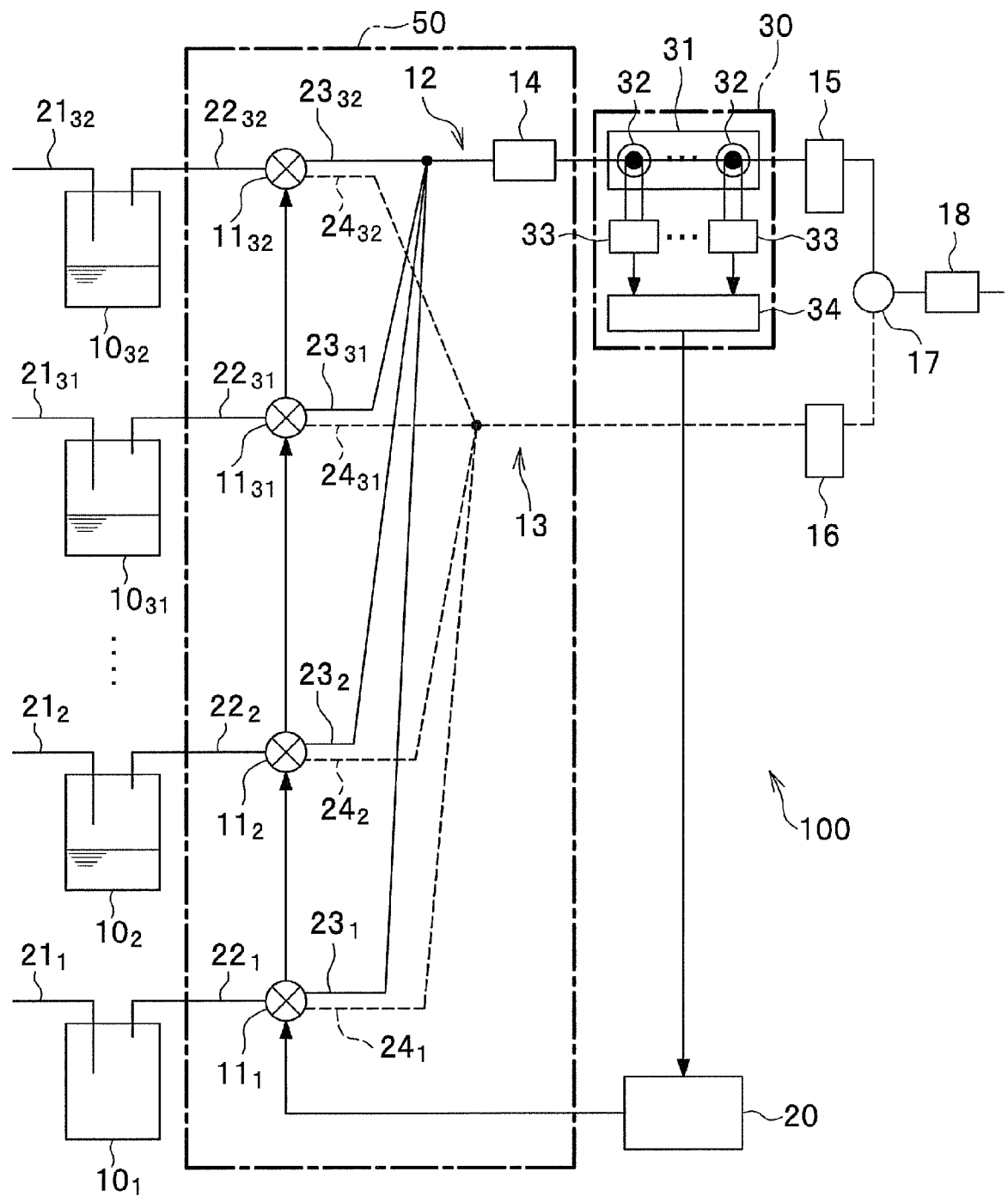
FIG. 1 is a diagram showing a structure of an odor blender according to a first embodiment.

| Description for reference characters | |
|---|---|
| 10 | sample container |
| $10_1$ | carrier gas container |
| $10_2$-$10_{32}$ | component odor container |
| 11, $11_1$-$11_{32}$ | solenoid valve |
| 12 | blend line |
| 13 | bypass line |
| 14 | blend part |
| 20 | computer (control unit) |
| 50, 50A, 50B | odor blending unit |
| 60 | blended odor measuring device |
| 70 | target odor measuring device |
| 100 | odor blender |
| 110, 110B | odor recorder |
| 120 | odor recording and reproducing system |

BEST MODE FOR CARRYING OUT THE INVENTION

Hereinbelow, embodiments of the present invention will be described below in detail with reference to the accompanying drawings.

First Embodiment

First, referring to FIG. 1, a first embodiment of an odor blender according to the present invention will be described. Herein, FIG. 1 is a diagram showing a structure of an odor blender according to the first embodiment.

(Entire Structure)

An odor blender 100 according to the first embodiment to which thirty-two sample containers $10_1$-$10_{32}$ are removably attached includes: an odor blending unit 50 having a blend line 12 with a blend part 14 configured to blend component odor gases or carrier gas supplied from the attached sample containers $10_1$-$10_{32}$, a bypass line 13 configured to discharge the component odor gases or carrier gas from the attached sample containers $10_1$-$10_{32}$, and solenoid valves $11_1$-$11_{32}$ configured to switch corresponding connections from the attached sample containers $10_1$-$10_{32}$ to between the blend line 12 and the bypass line 13; thirty-two sample containers $10_1$-$10_{32}$ (carrier gas container $10_1$ and component odor containers $10_2$-$10_{32}$) attached to the odor blending unit 50; a sensor part 30 (measuring unit) connected to a downstream of the blend part 14 on the blend line 12; valved flowmeters 15 and 16 (flow regulating unit) configured to adjust corresponding flow rates in the blend line 12 and the bypass line 13; a suction pump 17 (gas flow driving unit) configured to drive gas flows in the blend line 12 and the bypass line 13; a filter 18 (discharged gas collecting unit) configured to collect the discharged gases from the blend line 12 and the bypass line 13; and a computer 20 (control unit) configured to control, by the solenoid valves $11_1$-$11_{32}$, switching of the connections from the sample containers $10_1$-$10_{32}$ to between the blend line 12 and the bypass line 13, and at the same time, to receive a measured value (sensor output vector) from the sensor part 30.

Herein, the container $10_1$ is an empty sample container used as a carrier gas container, while the containers $10_2$-$10_{32}$ are component odor containers each containing a liquid which is to be a component odor gas. The sample containers $10_1$-$10_{32}$ are connected to a carrier gas source, such as air, through their corresponding piping $21_1$-$21_{32}$, and also connected to common ports of the corresponding solenoid valves $11_1$-$11_{32}$ through piping $22_1$-$22_{32}$. It should be noted that each of the solenoid valves $11_1$-$11_{32}$ is a 3-way solenoid valve having a common port, an NO (Normally Open) port and an NC (Normally Closed) port, in which the connection from the common port to between the NO port and the NC port is complementarily switched. When air is used as a carrier gas, the other ends of the piping $22_1$-$22_{32}$ are opened to the atmosphere.

The NC ports of the solenoid valves $11_1$-$11_{32}$ are connected to the blend line 12 (path shown with solid lines in the drawing). In other words, the NC ports of the solenoid valves $11_1$-$11_{32}$ are connected to the blend part 14 through their corresponding piping $23_1$-$23_{32}$, and then the blend part 14 is connected to the suction pump 17 through the valved flowmeter 15.

On the other hand, the NO ports of the solenoid valves $11_1$-$11_{32}$ are connected to the bypass line 13 (path shown with dotted lines in the drawing). In other words, the NO ports of the solenoid valves $11_1$-$11_{32}$ are connected to the suction pump 17 through their corresponding piping $24_1$-$24_{32}$ and then through the valved flowmeter 16.

It should be noted that the suction pumps 17 may be disposed separately on the blend line 12 and the bypass line 13, so that they drive the gas flows in the respective lines independently.

Next, each component of the odor blender 100 of the first embodiment will be described in detail.
(Odor Blending Unit)

To the odor blending unit 50, the sample containers $10_1$-$10_{32}$ including one carrier gas container $10_1$ and thirty-one component odor containers $10_2$-$10_{32}$ can be removably attached. The odor blending unit 50 is formed of: the blend part 14 configured to blend the carrier gas and the component odor gases supplied from the attached thirty-two sample containers $10_1$-$10_{32}$; the blend line 12 configured to lead the carrier gas and the component odor gases from the attached sample containers $10_1$-$10_{32}$ to the blend part 14; the bypass line 13 configured to discharge the carrier gas and the component odor gases from the attached sample containers $10_1$-$10_{32}$; and the solenoid valves $11_1$-$11_{32}$ configured to switch the corresponding connections from the attached sample containers $10_1$-$10_{32}$ to between the blend line 12 and the bypass line 13.

To the odor blending unit 50, the suction pump 17 is connected to a downstream side of the blend line 12 and the bypass line 13, through the valved flowmeter 15 and the valved flowmeter 16, respectively.
(Sample Container, Component Odor Container, and Carrier Gas Container)

The sample containers $10_1$-$10_{32}$ are classified into two groups: the carrier gas container $10_1$ for supplying a carrier gas; and the component odor containers $10_2$-$10_{32}$ for supplying component odor gases. In the present embodiment, one carrier gas container $10_1$ is provided relative to thirty-one component odor containers $10_2$-$10_{32}$.

For the sample containers $10_1$-$10_{32}$, a vial having a volume of about several ml to several tens ml can be used, and the piping $21_1$-$21_{32}$ for gas flow inlet and the piping $22_1$-$22_{32}$ for gas flow outlet are attached to the corresponding containers at the top portion thereof, each using a septum. The lengths of the piping $21_1$-$21_{32}$ for inlet and the piping $22_1$-$22_{32}$ for outlet are defined so that the opening of the piping is positioned in a headspace of each of the sample containers $10_1$-$10_{32}$ (a space above a surface of the liquid which is to be the component odor gas). It is preferred that the piping $21_1$-$21_{32}$ for inlet are made longer than the piping $22_1$-$22_{32}$ for outlet, and each opening of the piping $22_1$-$22_{32}$ is located at an upper portion of the headspace. By defining the piping for inlet and outlet as such, component odor gas generated in the component odor containers $10_2$-$10_{32}$ can be homogeneously supplied therefrom.

When any of the component odor containers $10_2$-$10_{32}$ do not supply component odor gases to the blend line 12, the carrier gas container $10_1$ communicates with the blend line 12 to supply the carrier gas and dilute the blended odor. In addition, the carrier gas container $10_1$ has the same configuration as those of the component odor containers $10_2$-$10_{32}$, in order to maintain a flow rate in each gas flow line constant, when connected to any of gas flow lines (the blend line 12 or the bypass line 13).

It should be noted that a single carrier gas container will suffice, but multiple carrier gas containers may be provided.

Examples of the carrier gas include odorless gas, such as air, dry air and nitrogen gas. Each of the piping $21_1$-$21_{32}$ for inlet connected to the corresponding sample containers $10_1$-$10_{32}$ has an end portion on an upstream side thereof connected to a supply source, such as a compressed gas cylinder containing a carrier gas. When the carrier gas is air, end portions on the upstream side of the piping $21_1$-$21_{32}$ are opened to the atmosphere, which serves as a supply source of the carrier gas.
(Solenoid Valve)

Each of the solenoid valves $11_1$-$11_{32}$ is a 3-way solenoid valve for switching connection from the corresponding sample containers $10_1$-$10_{32}$, to between the blend line 12 and the bypass line 13.

Figure 10:
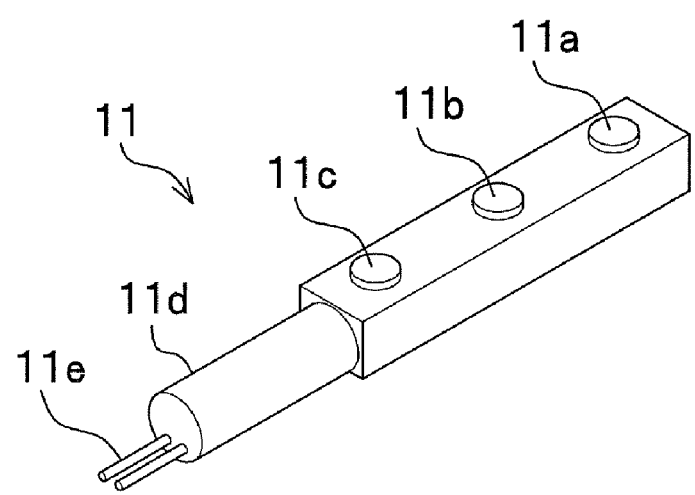
FIG. 10 is a perspective view showing a structure of a solenoid valve.

For the 3-way solenoid valve, for example, a solenoid valve LHDA122111H (product name) manufactured by The Lee Co. can be used. As shown in FIG. 10, the 3-way solenoid valve has a common port 11b, an NC port 11a, an NO port 11c, a solenoid 11d, an electrode 11e and the like, and switches the connection from the common port 11b to between the NC port 11a and the NO port 11c, in accordance with an application of voltage to the electrode 11e. When no voltage is applied to the electrode 11e, the common port 11b is connected to the NO port 11c; when voltage is applied to the electrode 11e, a current flows through the solenoid 11d, and a plunger (not shown) inside the valve is shifted, to connect the common port 11b with the NC port 11a.

The electrode 11e of each of the solenoid valves $11_1$-$11_{32}$ is connected to the computer 20, and works in accordance with a control signal from the computer 20.

In the first embodiment, the common port 11b serves as a gas inlet, and the piping $22_1$-$22_{32}$ attached to the corresponding sample containers $10_1$-$10_{32}$ are connected to the corresponding solenoid valves. In addition, to the NO ports 11c of the respective solenoid valves $11_1$-$11_{32}$ connected to the corresponding sample containers $10_1$-$10_{32}$, the corresponding piping $23_1$-$23_{32}$ leading to the bypass line 13 are connected, and to the NC ports 11a, the respective piping $24_1$-$24_{32}$ leading to the blend line 12 are connected.
(Gas Flow Driving Unit)

The suction pump 17 is a gas flow driving unit configured to generate gas flows in the blend line 12 and in the bypass line 13. When the suction pump 17 performs suction of the blend line 12 and the bypass line 13 through the valved flowmeters 15 and 16, respectively, the component odor gas or the carrier gas in the headspace of the sample containers $10_1$-$10_{32}$ are introduced to the blend line 12 or the bypass line 13 through the solenoid valves $11_1$-$11_{32}$.

Figure 2:
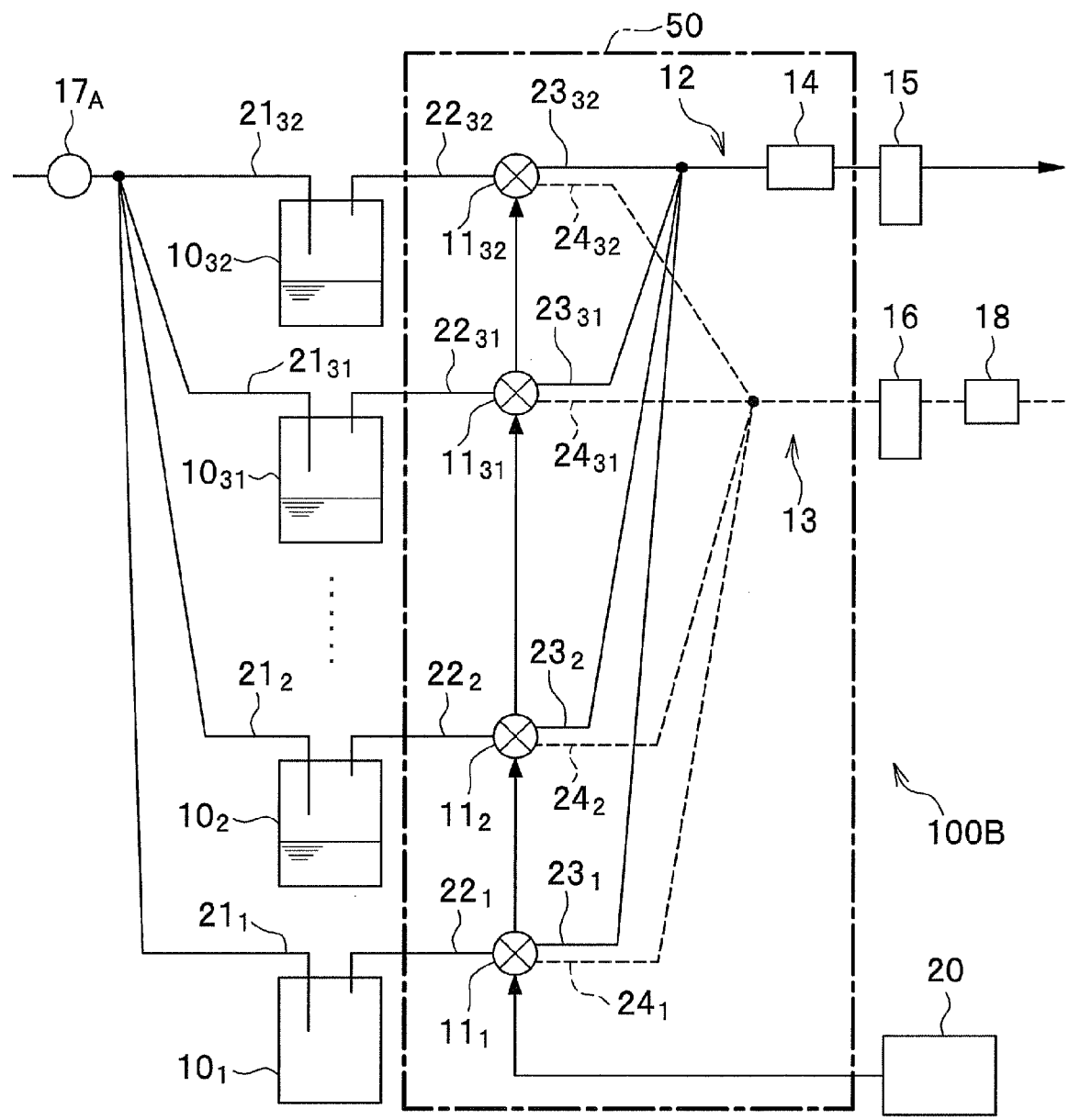
FIG. 2 is a diagram showing an odor blender according to a second embodiment.

In the first embodiment, as a gas flow driving unit, the suction pump 17 is provided downstream of the gas flow. Alternatively, like in other embodiments as shown in FIG. 2, a compressor 17A, a fan or the like may be provided on an upstream side, for supplying a pressurized carrier gas from the upstream side for driving the gas flow.

Alternatively, the suction pumps 17 may be separately disposed on each of the blend line 12 and the bypass line 13.
(Flow Regulating Unit)

The valved flowmeters 15 and 16 are flow regulating units provided on the respective gas flow lines and configured to retain the flow rate of the gas flow in the blend line 12 and the bypass line 13 at a constant value, respectively.

For the valved flowmeter, for example, a flowmeter RK-1950 (product name) manufactured by KOFLOC (Kojima Instruments Inc.) can be used.

The valved flowmeters 15 and 16 are disposed on the blend line 12 and the bypass line 13, respectively, and configured to equalize the flow rate in the headspace of each of the sample containers $10_1$-$10_{32}$ when the sample containers $10_1$-$10_{32}$ are connected to the blend line 12, and the flow rate in the headspace of each of the sample containers $10_1$-$10_{32}$ when the sample containers $10_1$-$10_{32}$ are connected to the bypass line 13. By adjusting the gas flow as such, when the sample containers $10_1$-$10_{32}$ are connected to the blend line 12 by the solenoid valves $11_1$-$11_{32}$, the component odor gas or carrier gas can be supplied to the blend line 12 at a constant flow rate, immediately after the switching of the connections.

(Control Unit)

The computer 20 is a control unit configured to perform a switching control of the solenoid valves $11_1$-$11_{32}$, in accordance with a predetermined mixing ratio of the component odor gases. For the computer 20, for example, general-purpose computer, such as notebook PC (Personal Computer), can be used, and by outputting a switching signal through an appropriate driver circuit and the like to the solenoid valves $11_1$-$11_{32}$, the connecting states of the solenoid valves $11_1$-$11_{32}$ can be switched independently of each other.

The odor blender 100 of the first embodiment also receives a measured value of the blended odor from the sensor part 30, and determines an allocation of time for the connection switching by the solenoid valves $11_1$-$11_{32}$, in such a manner that the measured value (sensor output vector) becomes equal to a target value (target vector) determined in advance. The allocated time for the connection switching by each of the solenoid valves $11_1$-$11_{32}$ corresponds to a mixing ratio (recipe) of the component odor gases. In other words, the present embodiment also functions as an odor recorder configured to determine an odor recipe.

For the target value, for example, there can be used a measured value (sensor output vector) of a target odor to be recorded, which has been measured by a measuring device equipped with the sensor part 30 or a sensor part having a similar structure, other than the measuring device of the present invention. The target odor can be reproduced by generating a blended odor based on the recipe determined relative to the target value set in the manner as mentioned above.

It should be noted that, when the measured value and the target value do not become equal by a single adjustment, the measurement and adjustment may be repeated to gradually adjust the allocation of time for switching connection for each of the solenoid valves $11_1$-$11_{32}$ until the value converges.

In addition, the apparatus can be used as an odor recording and reproducing apparatus that can record and reproduce odors, by making the computer 20 configured to store a determined recipe in a storing unit, such as a hard disc, mounted in the computer 20, read out the recipe from the storing unit as needed, and generate a blended odor by controlling the solenoid valves in accordance with the recipe.

For details of the method for determining a recipe, a reference can be made to Japanese patent application No. 2005-43072A entitled "SMELL REGENERATING AND RECORDING METHOD AND SMELL REGENERATING AND RECORDING APPARATUS", filed by the inventors of the present application.

(Discharged Gas Collecting Unit)

The filter 18 is a discharged gas collecting unit configured to collect the component odor gases from the suction pump 17 which had been supplied to the blend line 12 and the bypass line 13, in order to prevent unnecessary dispersion of the odor in the atmosphere. For the filter 18, for example, an activated carbon filter can be used, and components of the component odor gases can be collected through adsorption by activated carbon contained in the filter.

(Blend Line)

The blend line 12 is a gas flow line in which a gas flow is driven by the suction pump 17 as a gas flow driving unit, and has the blend part 14. The blend line 12 also has the valved flowmeter 15 on a downstream side, in order to retain the gas flow through the blend line 12 constant.

(Blend Part)

The blend part 14 is provided in the blend line 12, which is a space for blending the carrier gas and the component odor gases provided from the corresponding sample containers $10_1$-$10_{32}$ through the corresponding solenoid valves $11_1$-$11_{32}$.

In the first embodiment, the blend part 14 is provided on the blend line 12, separately from a flow path for the carrier gas and component odor gases (piping $23_1$-$23_{32}$) of the blend line 12. Alternatively, by sequentially connecting a series of piping for introducing the carrier gas and component odor gases to one flow path, while the introduced carrier gas and component odor gases pass the flow path, they are blended with other carrier gas and component odor gases. As a result, the flow path can serve the same function as that of the blend part 14.

(Bypass Line)

The bypass line 13 is a gas flow line connected to the sample containers $10_1$-$10_{32}$ which are not connected to the blend line 12, by the corresponding solenoid valves $11_1$-$11_{32}$. In other words, each of the sample containers $10_1$-$10_{32}$ must be connected to either of the blend line 12 or the bypass line 13, through the corresponding solenoid valves $11_1$-$11_{32}$.

Like the blend line 12, the valved flowmeter 16 is provided on the bypass line 13 on a downstream side, so as to retain the gas flow through the bypass line 13 constant.

(Measuring Unit)

The sensor part 30 is a measuring unit configured to measure an odor of the blended odor including the component odor gases supplied to the blend line 12, and formed of: a sensor cell 31 having multiple QCM sensors 32; oscillators 33 for vibrating the respective QCM sensors: and a frequency counter 34 configured to measure a frequency of each QCM sensor 32.

Each QCM sensor 32 has a sensitive film applied thereto, each having a different adsorption property relative to multiple component odor gas components, and in accordance with measured values (sensor output vectors) based on outputs from the QCM sensors 32, an odor can be quantitatively specified. The measured value (sensor output vector) obtained by the sensor part 30 is transmitted to the computer 20.

For the sensitive film applied to the QCM sensor 32, for example, OV-17, TCP, Apiezon L, PEG1000 and the like can be used. It should be noted that the number of the QCM sensors 32 and the types of the sensitive films can be appropriately selected depending on the types of the component odor gas to be used for blending. Alternatively, odor sensors other than the QCM sensor can be used.

(Operation of the Apparatus)

Next, with reference to FIG. 1, an operation of the odor blender 100 according to the first embodiment will be described.

(Entire Operation)

In the first embodiment, by driving the suction pump 17, gases are sucked to the downstream side, and gas flows to the odor blender 100 are driven. In the present embodiment, the valved flowmeters 15 and 16 are provided on the blend line 12 and the bypass line 13, respectively, and the flow rate of each of the gas flow lines is adjusted to a predetermined constant value.

End portions on the upstream side of the piping $21_1$-$21_{32}$ connected on the inlet side to the corresponding sample containers $10_1$-$10_{32}$ are opened to the atmosphere, and from these opening ends, air is introduced as a carrier gas. The carrier gas introduced to the component odor containers $10_2$-$10_{32}$ each containing a liquid to be a component odor gas, among from the sample containers, is sent to either the blend line 12 or the bypass line 13 through the corresponding solenoid valves $11_1$-$11_{32}$, together with the component odor gas which turned into a gas in the headspace. Herein, a connection time (time frame for the connection) of the solenoid valves $11_1$-$11_{32}$ to the blend line 12 is controlled by the computer 20 in accordance with the pre-determined mixing ratio of component odor gases.

It should be noted that each of the component odor containers $10_2$-$10_{32}$ is connected to either the blend line 12 or the bypass line 13, and in the component odor containers $10_2$-$10_{32}$, regardless of the connection state, there is always a gas flow at a constant flow rate. With this configuration, the gas concentration of the component odor gas in the headspace of any of the component odor containers $10_2$-$10_{32}$ is always retained constant, and when the component odor containers $10_2$-$10_{32}$ are connected to the blend line 12, a component odor gas with a constant gas concentration can be supplied.

Herein, the carrier gas or the component odor gas supplied from the sample containers $10_1$-$10_{32}$ connected to the blend line 12 through the corresponding solenoid valves $11_1$-$11_{32}$ are sent to the blend part 14 through the corresponding piping $23_1$-$23_{32}$. In the solenoid valves $11_1$-$11_{32}$, the connection time with the blend line 12 per unit time, such as per second, is controlled, and at one moment, one of the sample containers $10_1$-$10_{32}$ is connected to the blend line 12, and the corresponding component odor gas (or carrier gas) is supplied to the blend line 12. The component odor gases sequentially introduced to the blend line 12 per unit time are blended (mixed) in the blend part 14, to thereby obtain a blended odor. The gas flow in the blend line 12 is adjusted to be sufficiently small, relative to the time required for blending, in the blend part 14, the component odor gases supplied at a mixing ratio which is renewed every unit time.

The blended odor blended in the blend part 14 is introduced to the sensor cell 31 of the sensor part 30, and the component odor is measured and expressed as sensor output vectors sent from the multiple QCM sensors 32.

Alternatively, the sensor cell 31 may be made to have a capacity corresponding to the blend part 14, so that the sensor cell 31 itself has a function of the blend part 14.

The blended odor (gas) measured at the sensor part 30 flows through the valved flowmeter 15 and is discharged from the suction pump 17. In the present embodiment, when the apparatus is used as an odor recipe recording apparatus configured to obtain a mixing ratio (recipe) of component odor gases for reproducing sensor output vectors obtained in advance by the QCM sensors, component odor gas components of the blended odor are absorbed and collected by the activated carbon of the filter 18 without being dispersed in the atmosphere. From the filter 18, only the odorless carrier gas (air) is discharged.

On the other hand, since the bypass line 13 is a gas flow line for retaining the gas concentration of the component odor gas in the headspace of each of the component odor containers $10_2$-$10_{32}$ constant, the component odor gases introduced to the connected bypass line 13 through the corresponding piping $24_1$-$24_{32}$ flow through the valved flowmeter 16 without being blended or measured, and discharged from the suction pump 17 and collected by the filter 18.

When the first embodiment is used as an odor blender, the odor blended in the blend line 12 can be simply dispersed to the atmosphere, without being collected by the filter 18. On the other hand, the component odor gases discharged from the bypass line 13 should be collected, without being discharged to the atmosphere. For attaining this, for example, the suction pumps 17 for driving gas flow are separately provided on the blend line 12 and the bypass line 13, or the suction pump 17 has two separate lines provided therein. The blended odor discharged through the blend line 12 and the valved flowmeter 15 from the suction pump 17 can be dispersed in the atmosphere as-is, while the component odor gases discharged through the bypass line 13, the valved flowmeter 16 and other line of the suction pump 17 can be collected by the connected filter 18.

When the apparatus is used as an odor reproducer, the sensor part 30 is not necessary, since it is sufficient that the component odor gases are blended at a predetermined mixing ratio by controlling the solenoid valves $11_1$-$11_{32}$ with the computer 20.

Figure 6:
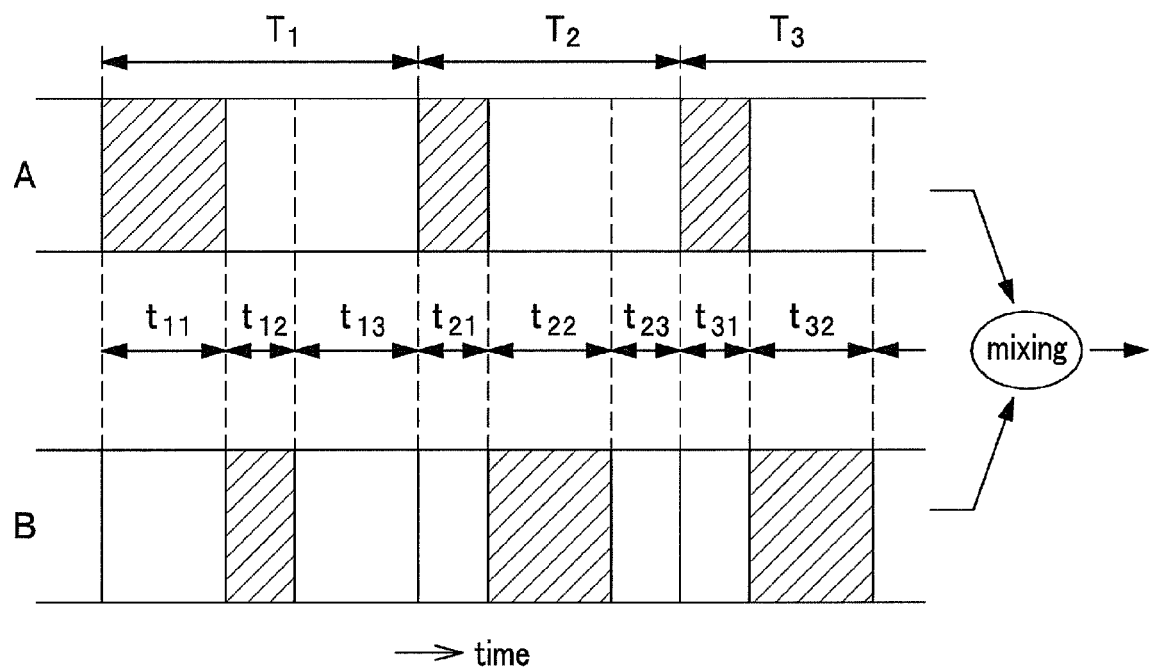
FIG. 6 is a diagram illustrating modes of supplying component odor gases in an odor blender according to a first embodiment.

Herein, with reference to FIGS. 1 and 6, the blending of the component odor gases by the odor blender 100 of the first embodiment will be described. FIG. 6 is a diagram illustrating modes of blending the component odor gases by the odor blender according to the first embodiment.

When the component odor gases to be used for blending are supplied to the blend line 12, in the odor blender 100 of the first embodiment, one or less container out of the component odor containers $10_2$-$10_{32}$ is connected to the blend line 12 at one moment. The connection time for each of the component odor containers $10_2$-$10_{32}$ with the blend line 12 is set in a manner of time division, in accordance with the mixing ratio of the component odor gases to be blended. In other words, the supply of each component odor gas is adjusted in such a manner that the predetermined mixing ratio is obtained by controlling the connection time per predetermined unit time.

FIG. 6 illustrates modes of supplying two different component odor gases A and B to the blend line. For the purpose easy understanding, herein, the odor blender 100 is simplified as to have three sample containers, including two component odor containers and one carrier gas container.

The unit time is set to approximately one second to several seconds, and each of T1-T3 indicates a period of unit time. In the time period T1, firstly during a time frame t11, a component odor container filled with the component odor gas A (hereinafter, referred to as "component odor container A") is connected to the blend line 12 by the corresponding solenoid valve, and the component odor gas A is supplied to the blend line 12. At this moment, a component odor container filled with the component odor gas B (hereinafter, referred to as "component odor container B") is connected to the bypass line 13, and the component odor gas supplied to the bypass line 13 is collected as discharged gas. The carrier gas container is connected to the bypass line 13.

In other words, one component odor container is connected to the blend line 12, while one carrier gas container and one component odor container are connected to the bypass line 13, so that the number of the component odor containers connected to the blend line 12 becomes equal to the number of the carrier gas containers connected to the bypass line 13. To put it another way, one sample container is connected to the blend line 12, while two sample containers are connected to the bypass line 13.

During next time frame t12, the component odor container A is connected to the bypass line 13, and at the same time the component odor container B is connected to the blend line 12, to thereby supply the blend line 12 with the component odor gas B. The carrier gas container is connected to the bypass line 13. Therefore, during the time frame t12, one component odor container is connected to the blend line 12, while one carrier gas container and one component odor container are connected to the bypass line 13, so that the number of the component odor containers connected to the blend line 12 becomes equal to the number of the carrier gas containers connected to the bypass line 13.

To put it another way, one sample container is connected to the blend line 12, while two sample containers are connected to the bypass line 13.

During next time frame t13, both the component odor containers A and B are connected to the bypass line 13, and the carrier gas container is connected to the blend line 12. When the carrier gas container is connected to the blend line 12, the carrier gas is supplied to the blend line 12, and thus the blended odor is diluted. Therefore, by controlling the time for connecting the carrier gas container with the blend line 12 per unit time, the entire concentration of the blended odor can be adjusted.

Also during the time frame t13, no component odor container is connected to the blend line 12, while no carrier gas container and two component odor containers are connected to the bypass line 13, so that the number of the component odor containers connected to the blend line 12 becomes equal to the number of the carrier gas containers connected to the bypass line 13.

To put it another way, one sample container is connected to the blend line 12, while two sample containers are connected to the bypass line 13.

The time period T1 of the unit time is divided into three time frames, t11, t12 and t13. The component odor gas A, component odor gas B and carrier gas supplied to the blend line 12 are blended (mixed) in the blend part 14, and a blended odor is generated.

In addition, the connection is controlled in such a manner that, at any divided time, the number of the component odor containers connected to the blend line 12 becomes equal to the number of the carrier gas containers connected to the bypass line 13. To put it another way, at any divided time, the number of the sample containers connected to the blend line 12 and the bypass line 13 become 1 and 2, respectively, and thus a load on each gas flow line does not change, leading to a constant flow rate regardless of the connection mode of the sample containers.

In the next time period T2 of unit time, during a time frame t21, the component odor container A is connected to the blend line 12, and thus the component odor gas A is supplied to the blend line 12. The component odor container B and the carrier gas container are connected to the bypass line 13.

During next time frame t22, the component odor container B is connected to the blend line 12, and thus the component odor gas B is supplied to the blend line 12. The component odor container A and the carrier gas container are connected to the bypass line 13.

During next time frame t23, the carrier gas container is connected to the blend line 12, and thus the carrier gas is supplied to the blend line 12. The component odor container A and the component odor container B are connected to the bypass line 13.

The component odor gas A, component odor gas B and carrier gas supplied in time-divided manner in the period T2 are mixed in the blend part 14, and a blended odor is generated.

After the time period T3, likewise, in accordance with the mixing ratio of the component odor gases, the connection time between each component odor container and the blend line 12 is renewed per unit time, to thereby generate blended odor. It should be noted that, without changing allocation of time frame for connection of each sample container with the blend line 12 per unit time, the same blended odor can be generated for a long period of time, by repeating the connection of each sample container with the blend line 12 per unit time.

In addition, by making a length of the connection time of a specific component odor container, e.g., component odor container A, with the blend line 12 equal to a length of the time period, there can be generated a blended odor that has a gas concentration equal to that of the component odor gas A in the headspace of the component odor container A.

The case in which one carrier gas container is present has been described above. Alternatively, a plurality (P) of the carrier gas containers may be present, with the proviso that Q>P where Q denotes the number of the component odor containers.

When P carrier gas containers are used, P component odor containers can be connected to the blend line 12 at the same time. When the number of the component odor containers connected to the blend line at the same time is R ($0 \leq R \leq P$), and the number of the carrier gas containers connected to the bypass line 13 is R, the number of the carrier gas containers connected to the blend line 12 is (P−R), and the number of the component odor containers connected to the bypass line 13 is (Q−R). Therefore, the total number of the sample containers connected to the blend line 12 is obtained as (R+(P−R))=P, while the total number of the sample containers connected to the bypass line 13 is obtained as ((Q−R)+R)=Q, which shows that the number of the sample containers connected to the blend line 12 and the number of the sample containers connected to the bypass line 13 are constant, regardless of the number of the component odor containers connected to the blend line 12.

Accordingly, by controlling the connection state in such a manner that the number of the component odor containers connected to the blend line 12 at the same time becomes equal to the number of the carrier gas containers connected to the bypass line 13, the number of the sample containers connected to the blend line 12 becomes P and the number of the sample containers connected to the bypass line 13 becomes Q at any time frame. Since the load in each gas flow lines does not change, each flow rate becomes constant, and as a result, the component odor gas can be stably supplied to the blend line 12.

In the first embodiment, the supply of the component odor gases to be used in blending is controlled in terms of the connection time per unit time, between the corresponding component odor container and the blend line 12. Accordingly, when the number of the types of component odor gas to be used in blending a single odor becomes larger, it is necessary that a predetermined unit time be finely divided, and at the same time, that the switching of the connections by the solenoid valves be performed with highly accurate time periods, in order to supply the component odor gas at a predetermined mixing ratio with accuracy. In other words, the switching of the connections by the solenoid valves should be performed at a high speed. A solenoid valve meeting such a high-speed demand is expensive, which in turn makes the odor blender expensive.

Therefore, by increasing the number of the carrier gas containers, a response speed required in the solenoid valve can be reduced. For example, when the number is P, the number of the component odor containers that can be connected to the blend line 12 at the same time is P, and thus there can be allocated the connection time which is P times as long as the connection time for the case where the number of the component odor containers that can be connected at the same time is one. In other words, the response speed required in the solenoid valve can be reduced to 1/P.

However, when the number of the sample contains connected at the same time is set to P, the gas concentration of the component odor gas supplied from each component odor container becomes 1/P, at most, of the gas concentration in the headspace, and therefore, the number of the carrier gas containers can be appropriately selected in accordance with a type of the component odor gas for blending a single odor and a maximum concentration of each component odor gas. In the present embodiment, the carrier gas container and the component odor container are the sample container having the same shape. Therefore, if necessary, the sample containers may be appropriately used as an arbitral combination of the carrier gas containers and the component odor containers.

Figure 11:
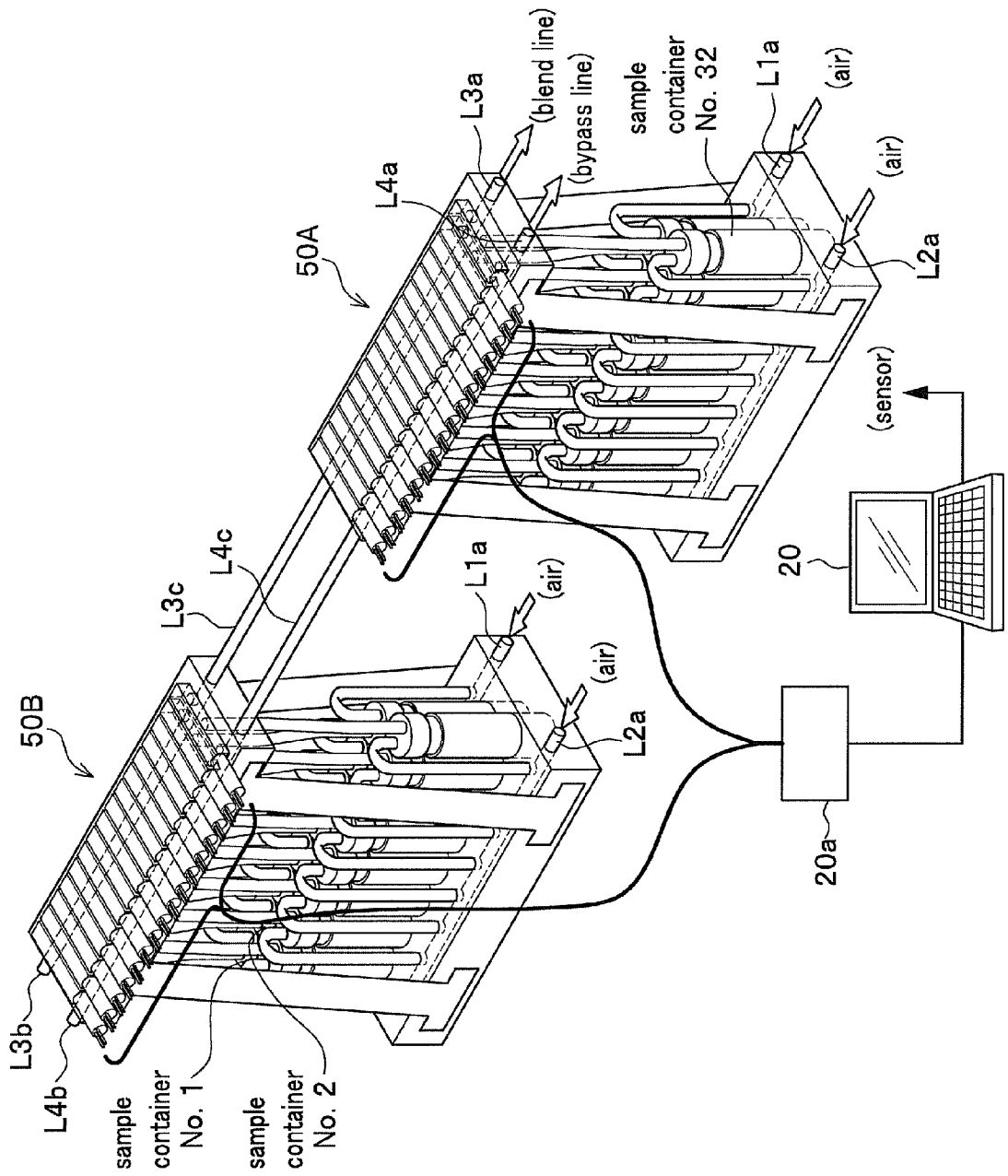
FIG. 11 is a diagram showing a structure of an odor blender of an example.

In addition, for example, like the odor blender shown in FIG. 11, when multiple odor blending units (50A, 50B) each capable of mounting sixteen sample containers are used in combination, one carrier gas container may be present per odor blending unit.

As described above, according to the odor blender 100 of the first embodiment, by using a smaller number of the carrier gas containers than the number of the component odor containers, a blended odor can be generated at a stable mixing ratio, and the number of the types of component odor gas to be used at the same time can be increased without making the size of the apparatus larger. In addition, since the number of the carrier gas containers can be reduced smaller than that of the component odor container, in the production of the blended odor, the maximum concentration of the component odor gas can be made higher.

Second Embodiment

Next, referring to FIG. 2, a second embodiment of an odor blender 100B will be described. Herein, FIG. 2 is a diagram showing a structure of an odor blender according to the second embodiment.
(Structure)

The structure of the present embodiment is different from that of the odor blender 100 of the first embodiment shown in FIG. 1 in that, a compressor 17A is provided as a gas flow driving unit on an upstream side and a gas flow is driven into the apparatus by supplying a pressurized carrier gas from the upstream side, that there is no sensor part provided, and that the filter 18 is provided so as to collect only the discharged gas from the bypass line 13.

Other configurations are substantially the same as in the first embodiment, thus a duplicate description is omitted.

In the odor blender 100B of the second embodiment, the compressor 17A is provided as a gas flow driving unit on an upstream side. The pressurized carrier gas from the compressor 17A is supplied to the odor blender 100B, through the piping $21_1$-$21_{32}$ connected to an inlet side of the corresponding sample containers $10_1$-$10_{32}$.

On the downstream side of the blend line 12, the valved flowmeter 15 is provided, and a downstream end is opened to the atmosphere. On the other hand, on the downstream side of the bypass line 13, the valved flowmeter 16 is provided, and a downstream end is connected to the filter 18.

When air is used as a carrier gas, a supply side of the compressor 17A is opened to the atmosphere. When another gas is used as a carrier gas, a gas supply source, such as a compressed gas cylinder of the carrier gas may be connected to the supply side of the compressor 17A. As a gas flow driving unit, a fan may be used, other than the compressor.
(Operation)

Next, the operation of the second embodiment will be described. In the odor blender 100B of the second embodiment, the compressor 17A is provided as a gas flow driving unit on an upstream side, and by supplying a pressurized carrier gas through the piping $21_1$-$21_{32}$, a gas flow is generated in the odor blender 100B.

By the carrier gas supplied through the piping $21_1$-$21_{32}$, the carrier gas or the component odor gases in the sample containers $10_1$-$10_{32}$ are supplied to the blend line 12 or the bypass line 13, depending on the connection state of the solenoid valves $11_1$-$11_{32}$. Switching of the connection modes of the solenoid valves $11_1$-$11_{32}$ is controlled by the computer 20, in accordance with the predetermined mixing ratio (recipe). The component odor gases and the carrier gas supplied to the blend line 12 in accordance with the recipe are blended in the blend part 14, and the blended odor is generated. The odor blended in the blend part 14 is dispersed in the atmosphere through the valved flowmeter 15.

On the other hand, the component odor gases supplied to the bypass line 13 are discharged through the valved flowmeter 16 and collected by the filter 18, and solely the carrier gas is discharged to the atmosphere.

The second embodiment is configured in such a manner that the blended odor is dispersed to the atmosphere, and the blended odor is synthesized by the computer 20 in accordance with the recipe. The apparatus can be used as an odor reproducer which disperses the blended odor to the atmosphere and supplies the blended odor to a person nearby the apparatus.

When the apparatus is used as an odor reproducer which disperses the blended odor to the atmosphere, it is preferred that the gas flow driving unit be provided on an upstream side of the gas flow line, as in the second embodiment. When the suction pump 17 is provided on a downstream side of the gas flow line as in the first embodiment shown in FIG. 1, the blended odor is dispersed to the atmosphere through the suction pump 17. With such a structure, there may be a problem that the gas component of the odor blended before may be adsorbed by the suction pump 17, or absorbed by oils or the like used in the suction pump 17, and an odor newly blended may be mixed with such gas components remaining in the suction pump 17, leading to deterioration of the blended odor.

This problem of remaining gas components may occur in the valved flowmeter 15 and the blend part 14, in addition to the suction pump 17. However, as compared with the suction pump 17, such parts do not use a material, such as oil, which tends to retain gas components, and washing thereof is easy. Therefore, when the pressurized carrier gas is introduced from an upstream side of the gas flow line as in the second embodiment, the component odor gas components hardly remain on the downstream side of the blend part 14, and the second embodiment is especially preferred as an odor reproducer.

Third Embodiment

Figure 3:
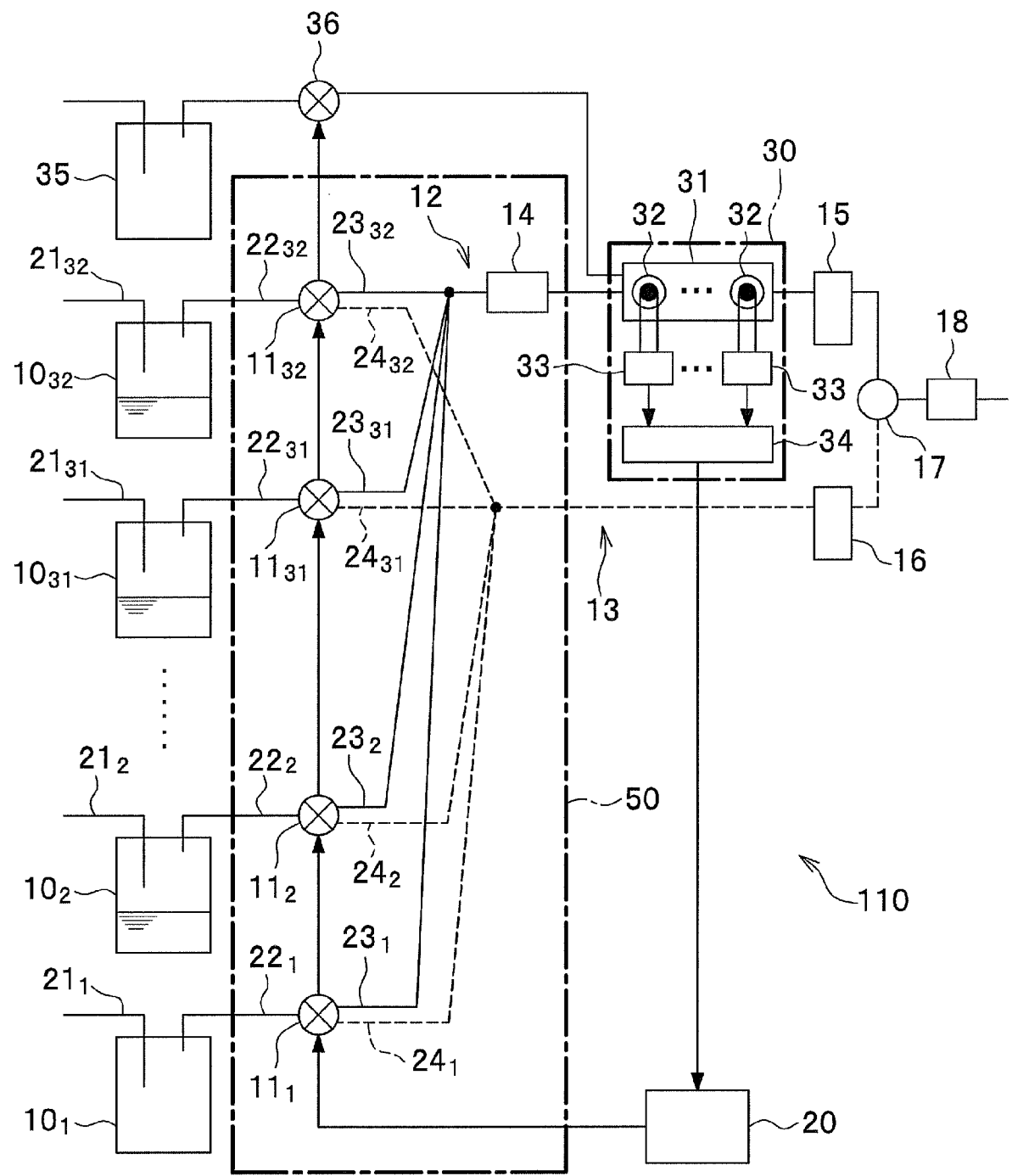
FIG. 3 is a diagram showing a structure of an odor recorder according to a third embodiment.

Next, referring to FIG. 3, a third embodiment will be described. Herein, FIG. 3 is a diagram showing a structure of an odor recorder according to the third embodiment.

(Structure)

In addition to the odor blender 100 of the first embodiment shown in FIG. 1, an odor recorder 110 of the third embodiment has a sample container 35 for containing a target odor gas to be recorded, in which the target odor gas is supplied to the sensor part 30 through the solenoid valve 36.

Other configurations are substantially the same as in the first embodiment, and thus a duplicate description is omitted.

(Operation)

Next, the operation of the odor recorder 110 of the third embodiment will be described.

In the odor recorder 110 of the third embodiment, first, the suction pump 17 is driven, the solenoid valve 36 is opened, and a target odor gas is supplied to the sensor cell 31 of the sensor part 30 from the sample container 35, to thereby measure the target odor. It should be noted that, during the measurement of the target odor, the component odor containers $10_2$-$10_{32}$ are connected to the bypass line 13, and the carrier gas container $10_1$ is connected to the blend line 12. Alternatively, the carrier gas container may be connected to the bypass line 13 so as not to dilute the target odor gas.

The target odor gas supplied to the sensor cell 31 is measured with the multiple QCM sensors 32, and the measured value is transmitted as a sensor output vector to the computer 20.

After the completion of the measurement of the target odor, the computer 20 closes the solenoid valve 36, adjusts the connection time of the component odor containers $10_2$-$10_{32}$ and the carrier gas container $10_1$ with the blend line 12, measures with the sensor part 30 the odor blended in the blend part 14, and obtains a mixing ratio (recipe) of the component odor gases for reproducing the measured value of the target odor. The procedures for obtaining the mixing ratio (recipe) of the component odor gases for reproducing the measured value of target odor is substantially the same as in the first embodiment, except that a preset measured value of the target odor is used instead of the measured value of the target odor, and thus a duplicate description is omitted.

In other words, the third embodiment can serve as an odor recorder which determines a recipe for reproducing a target odor.

Fourth Embodiment

Figure 4:
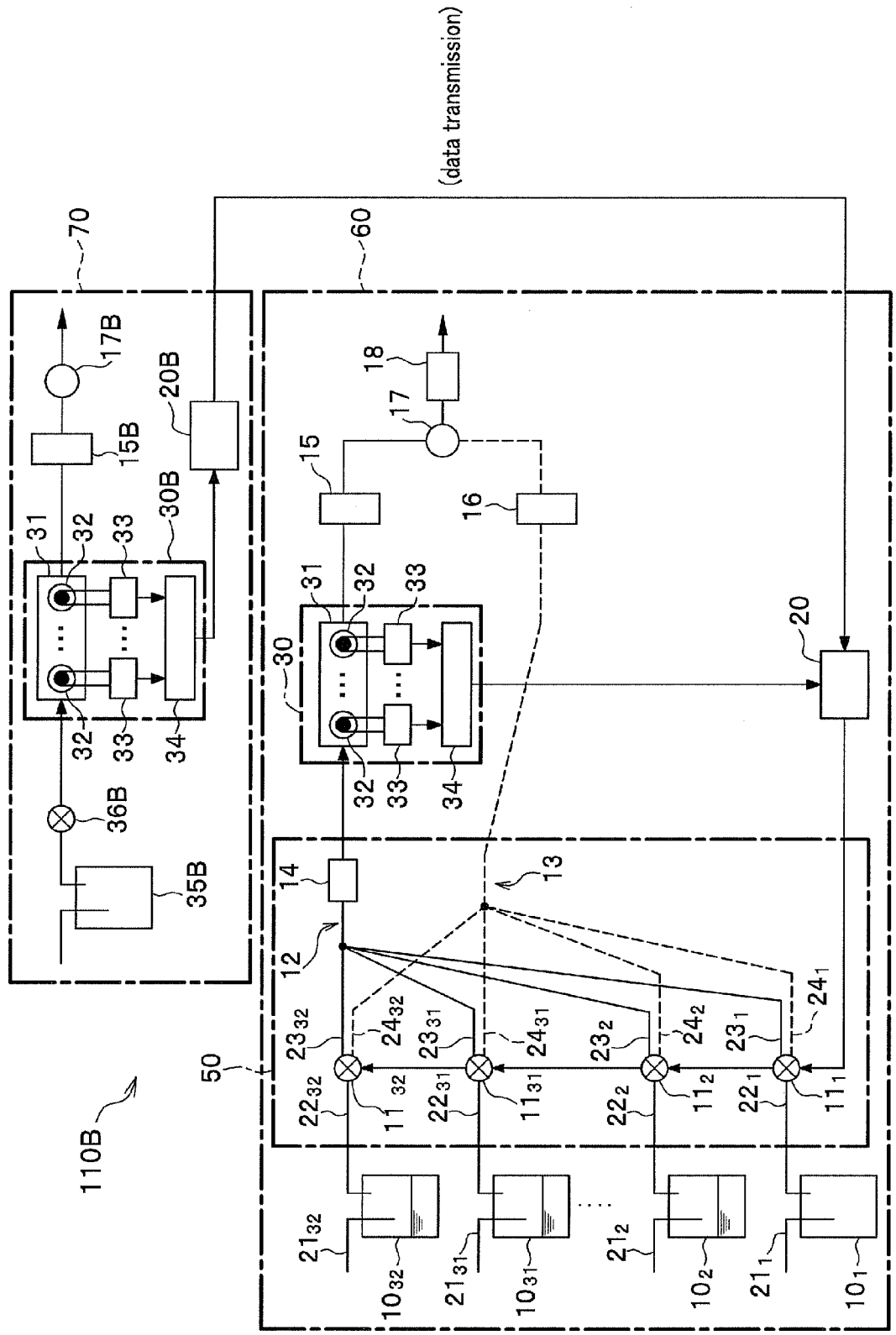
FIG. 4 is a diagram showing a structure of an odor recorder according to a fourth embodiment.

Next, referring to FIG. 4, an odor recorder according to a fourth embodiment will be described. Herein, FIG. 4 is a diagram showing a structure of an odor recorder according to the fourth embodiment.

(Structure)

An odor recorder 110B of the fourth embodiment is formed of a target odor measuring device 70 and an odor blender 60, and a computer 20B of the target odor measuring device 70 and the computer 20 of the odor blender 60 are connected to each other so as to be capable of data transmission. Herein, the expression "connection which is capable of data transmission" intends to include, for example, a direct connection through a signal cable, and an indirect connection through a network system, such as LAN (Local Area Network), wireless communication and the like.

The target odor measuring device 70 has a sample container 35B for storing a target odor gas and is configured to supply the target odor gas to a sensor part 30B through a solenoid valve 36B. Since the sensor part 30B has substantially the same structure as that of the sensor part 30 of the first embodiment, a duplicate description is omitted. There are provided a suction pump 17B as a gas flow driving unit configured to lead the target odor gas to the sensor cell 31 of the sensor part 30B, and a valved flowmeter 15B configured to adjust a flow rate of the gas flow, on an upstream side of the suction pump 17B.

The odor blender 60 has substantially the same structure as that of the odor blender 100 of the first embodiment shown in FIG. 1, except that a function of receiving a measured value of the target odor is added to the computer 20, and thus a duplicate description is omitted.

(Operation)

In the odor recorder 110B of the fourth embodiment, first, a target odor is measured using the target odor measuring device 70. The target odor measuring device 70 drives a gas flow by driving the suction pump 17B and opens the solenoid valve 36B, to thereby lead the target odor gas stored in the sample container 35B to the sensor cell 31 of the sensor part 30B. The target odor gas introduced to the sensor cell 31 is measured with the multiple QCM sensors 32, and the measured value is transmitted as a sensor output vector to the computer 20B. The computer 20B transmits the measured value of the target odor to the computer 20 of the odor blender 60.

Based on the measured value of the target odor transmitted from the target odor measuring device 70, the odor blender 60 obtains a mixing ratio (recipe) of the target odor gas for reproducing the measured value. The procedures for obtaining the recipe for reproducing the measured value (sensor output vector) are substantially the same as in the first embodiment, and thus a duplicate description is omitted.

In the odor recorder 110B of the fourth embodiment, the structure for measuring the target odor and the structure for obtaining the recipe from the measured value are separated, and the value measured by the target odor measuring device 70 is transmitted to the odor blender 60 for obtaining the recipe. Therefore, the target odor can be measured with the target odor measuring device 70 having a simple structure, resulting in less limitation in the setting location of the apparatus, and various types of the target odor can be recorded as the measured value of odor. Since the recipe corresponding to the target odor is determined based on the measured value of the target odor transmitted as data, the odor blender 60 having relatively large size can be set and used in a laboratory or the like.

Fifth Embodiment

Next, referring to FIG. 5, an odor recording and reproducing system 120 according to a fifth embodiment will be described. Herein, FIG. 5 is a diagram showing a structure of an odor recording and reproducing system according to a fifth embodiment.

(Structure)

Figure 5:
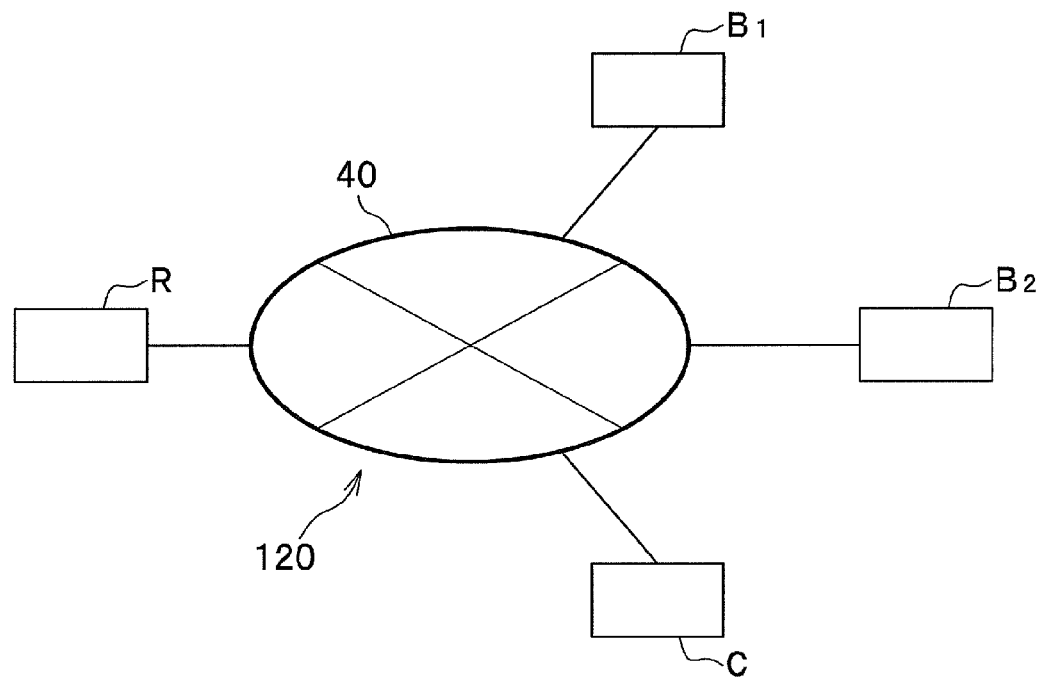
FIG. 5 is a diagram showing a structure of an odor recording and reproducing system according to a fifth embodiment.

The odor recording and reproducing system 120 according to the fifth embodiment shown in FIG. 5 is formed of an odor recorder R, odor reproducers B1 and B2, and a management computer C. The odor recorder R and the odor reproducers B1 and B2 are connected to the management computer C through a network system 40.

Herein, the odor recorder R includes the odor recorder 110 of the third embodiment or the odor recorder 110B of the fourth embodiment, and further includes a unit for communicating through the network system 40. Each of the odor reproducers B1 and B2 includes the odor blender 100B of the second embodiment, and further includes a unit for communicating through the network system 40.

For the management computer C, there can be mentioned a general-purpose computer having a CPU (central processing unit), memory such as RAM and ROM, recording unit such as hard disc, and a unit for communicating through the network, such as a network adapter.

It should be noted that the numbers of the odor recorder, the odor reproducer and the management computer forming the odor recording and reproducing system 120 of the fifth embodiment is not limited to the numbers shown in FIG. 5, and any number can be used.

(Operation)

The management computer C obtains, through the network system 40, an odor recipe (mixing ratio of the component odor) that has been collected by the odor recorder R, and stores and manages the recipe in a recording medium, such as a hard disc. Through the network, the odor reproducer B1 or B2 can request the odor recipe to the management computer C and receives the odor recipe therefrom. The odor reproducer B1 or B2 generates the blended odor based on the odor recipe obtained from the management computer C, and disperses the blended odor to the atmosphere.

In addition, the management computer C may control the operation of the odor reproducer B1 or B2, so as to generate a blended odor based on the recipe sent from the management computer C, and to disperse the blended odor to the atmosphere.

As one application of the apparatus, in hotels or hospitals, for example, an odor reproducer B1 or the like may be placed in each room. Each odor reproducer B1 or the like is controlled by the management computer C set in a management office of the hotel or hospital through a network unit (network system), to thereby supply an odor in accordance with the request of a stayer of the room or a condition of a patient. In movie theaters or the like, with a use of a portable odor reproducer B1 or the like checked out per viewer, an odor can be supplied in synchronization with a motion picture, such as an animated film.

Sixth Embodiment

Next, another embodiment of the odor blender of the present invention will be described.

In the odor blender of the sixth embodiment, the odor blending unit, the sample container, the component odor container, the carrier gas container, the solenoid valve, the gas flow driving unit, the flow regulating unit, the control unit, the discharged gas collecting unit, the blend line, the blend part, the bypass line and the measuring unit have the same structure as those of the first embodiment, except a variation in the control by the computer (control unit) of the connection from the component odor container to the blend line by opening and closing of the solenoid valves, and thus a duplicate description is omitted.

The odor blender of the sixth embodiment is the same as the first embodiment in that one component odor i is sent out at one moment. However in the sixth embodiment, the component odor sent out is re-selected every unit time $\tau$. In other words, the component odor container connected to the blend line 12 is selected so that the component odor is picked up whose concentration has the largest difference from the preset concentration at the present moment, and the picked-up component odor is supplied to the blend line 12 at the present moment. Therefore, a kind of the component odor sent out is different every unit time $\tau$.

When $xi(t)$ represents a preset concentration of a component odor i (component odor gas supplied from the component odor container 10$i$) at the present moment t, and $yi(t)$ represents an average concentration, the computer 20 (control unit) selects, every predetermined unit time $\tau$, a single component odor container 10$j$ that supplies the component odor gas with which $xi(t)$ becomes larger than $yi(t-1)$ and a relative error of both becomes the maximum. The computer 20 opens the solenoid valve 11$j$ corresponding to the selected component odor container 10$j$ and connects the selected component odor container 10$j$ to the blend line 12. Herein, the unit time $\tau$ is appropriately determined (e.g., 10 ms) in accordance with the time resolution required for the odor output from the odor blender. Therefore, among thirty-two solenoid valves $11_1$-$11_{32}$ in the odor blender 100 shown in FIG. 1, only one solenoid valve is opened during a unit time $\tau$. Accordingly, a ratio of the duration for opening the solenoid valve in a repeated time period to the repeated time period is a relative concentration of the component odor i.

Specifically, when $xi(t)$ represents the preset concentration of the component odor i (component odor gas supplied from the component odor container 10$i$) at the present moment t, and $yi(t)$ represents a ratio of the connection of the component odor to the blend line 12 during past time periods $n\tau$ (wherein n is a positive integer) from the time t, the computer 20 (control unit) selects, every predetermined unit time $\tau$, a single component odor container 10$j$ that supplies the component odor gas with which $xi(t)$ becomes larger than $yi(t-1)$ and the relative error $(xi(t)-yi(t-1))/xi(t))$ becomes the maximum. The computer 20 opens the solenoid valve 11$j$ corresponding to the selected component odor container 10$j$ and connects the selected component odor container 10$j$ to the blend line 12.

Herein, when there is no corresponding component odor, at the moment t, only the carrier gas container is connected to the blend line 12. With this configuration, there is an advantage that, when the actual concentration becomes higher than the preset concentration, the actual concentration is reduced to near the preset concentration.

Figure 17:
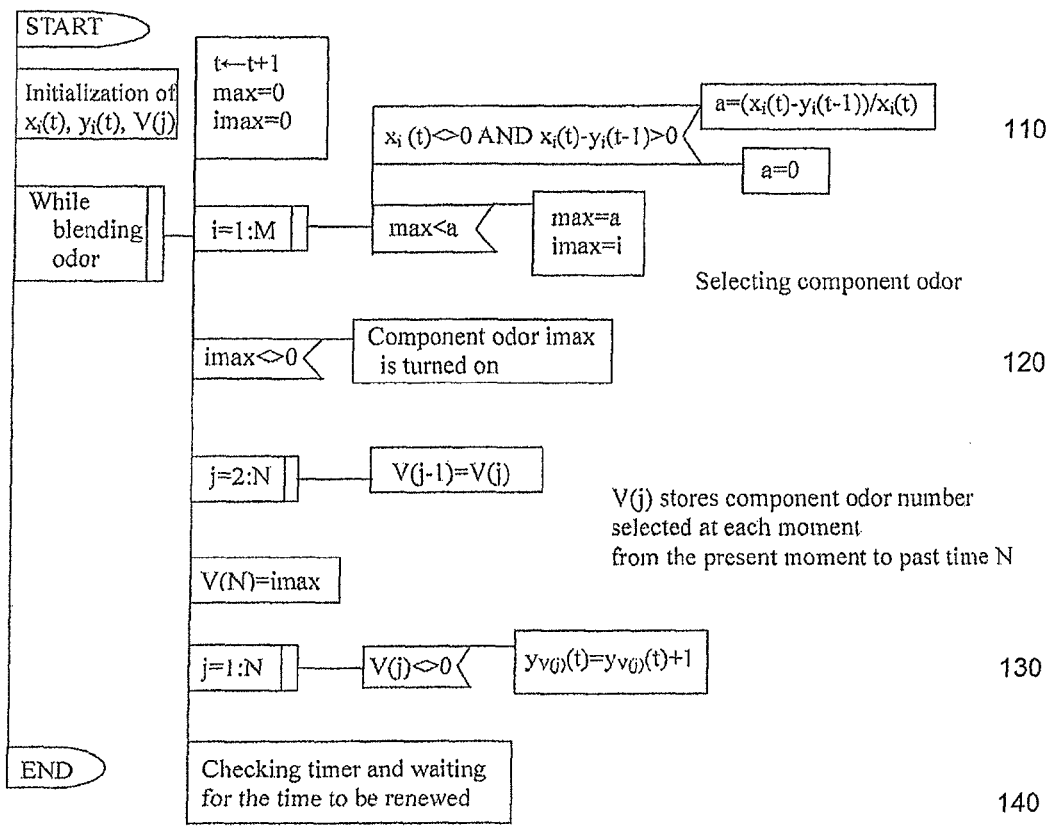
FIG. 17 is a flowchart of computer control of odor blending in accordance with an embodiment of the present invention.

A flowchart of the control by the computer 20 (control unit) of the odor blender is shown in FIG. 17.

In this flowchart, $xi(t)$ represents a preset concentration of the component odor i at the moment t, and $yi(t)$ represents a ratio of the component odor i turned on for past n time periods. $yi(t)$ may be considered as a value obtained by filtering a time change for ON/OFF of the solenoid valve corresponding to the component odor i, with an n-th order moving average filter. M represents the number of the component odors.

In the first loop, the component odor imax with which $yi(t)$ has the largest difference from $xi(t)$, i.e., the component odor imax with the largest relative error, is extracted (step 110), and the solenoid valve corresponding to the extracted component odor is turned on (step 120). In the subsequent two loops, $yi(t)$ is re-calculated to adjust time (step 130), and when the next time is reached, the procedure returns to the beginning of the While loop (step 140), and the similar process is repeated.

If there is a component odor with an excessively high value, unselecting the component odor gradually reduces the concentration.

In the sixth embodiment, a homogeneous odor blending can be attained with a high time resolution. With this odor blender, by supplying the odor to the odor sensor having a high time resolution, such as about 1/8 second or 1/16 second order, while dynamically changing the odor, a transient response of the odor sensor can be accurately measured. In addition, the process of actually diffusing the odor in the atmosphere can be more accurately regenerated. In the first embodiment described above, when the smaller duration than the repeated time period is considered, the component odor concentration is not homogeneous, and at a specific time, an odor with a high concentration is output. When the odor sensor is used for odor measurement, there may be a case where a higher time resolution is required. For example, when an odor spread in the atmosphere, the odor concentration shift to a large extent and a time resolution with an order of second is not sufficient. Accordingly, in a sensor system for capturing such an odor, a higher time resolution is required, and the present inventors developed a frequency veering measurement system with a time resolution of ⅛ second or 1/16 second, and uses in experiments. When a transient response of such an odor sensor is studied, the odor is supplied to the sensor of the odor blender while dynamically changing the odor, but a time resolution is not sufficient in a case of a PWM type odor blending. In this case, odor blender of the sixth embodiment odor blender is suitable.

EXAMPLE (Structure)

Figure 7:
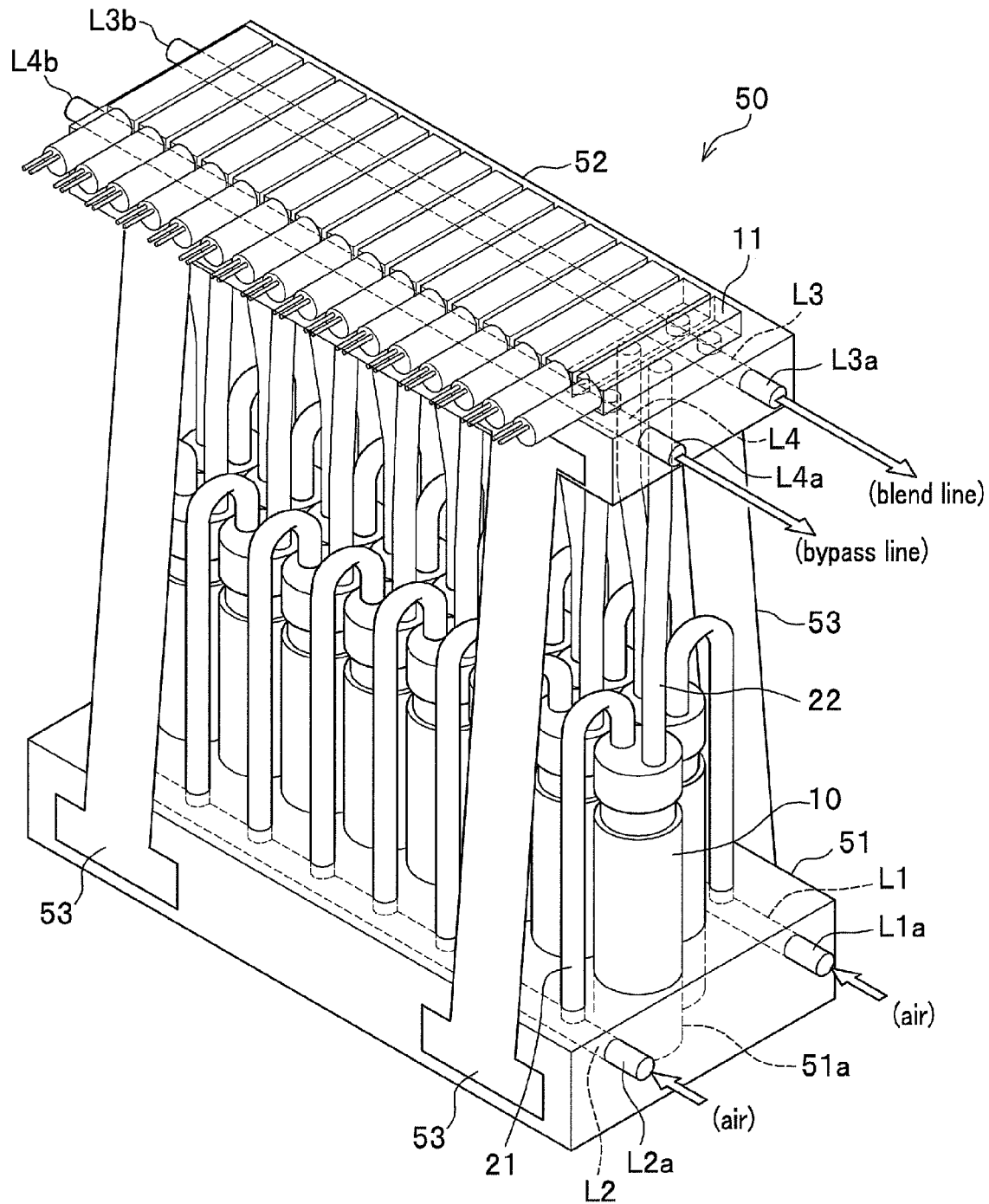
FIG. 7 is a perspective view showing a structure of an odor blending unit used in an odor blender of an example.

Next, with reference to FIGS. 7 to 11, a practical example of the odor blender of the first embodiment will be described. Herein, FIG. 7 is a perspective view showing a structure of an odor blending unit used in an odor blender of the example. FIG. 8 shows a lower manifold of the odor blending unit shown in FIG. 7, in which (a) is a plan view seen from above, (b) is a side view seen from the front. FIG. 9 shows an upper manifold of the odor blending unit shown in FIG. 7, in which (a) is a plan view seen from above, and (b) is a side view seen from the front. FIG. 10 is a perspective view showing a structure of a solenoid valve used in the odor blender of the example. FIG. 11 is a diagram showing a structure of the odor blender of the example.

First, the odor blending unit (manifold) 50 shown in FIG. 7 will be described. The odor blending unit 50 includes: channels L1 and L2 configured to supply the carrier gas; a lower manifold 51 having recesses 51a and the like configured to hold sixteen sample containers 10; an upper manifold 52 having the channel L2 as the blend line, a channel L3 as the bypass line, and the like; sixteen solenoid valves 11 aligned on an upper face of the upper manifold 52. The lower manifold 51 and the upper manifold 52 are integrally connected through four columns 53.

The lower manifold 51 made of brass has two rows of staggered recesses 51a, with each row containing eight recesses 51a each of which removably holds the sample container 10. In the lower manifold 51, the channels L1 and L2 for supplying the carrier gas are formed, and in the channels L1 and L2, eight channels R1 and eight channels R2 are formed, respectively, in such a manner that the channels L1 and R1 (L2 and R2) communicate with each other. Each channel R1 and each channel R2 have a hollow protrusion R1a and a hollow protrusion R2a, respectively, at upper end portions.

The channel L1 and the channel L2 have a hollow protrusion L1a and a hollow protrusion L2a are formed, respectively, at front end portions thereof.

In the upper manifold 52 made of brass, a channel L3 as the blend line and a channel L4 as the bypass line, both extending in a longitudinal direction, are formed. At a front end portion and a rear end portion of the channel L3, a hollow protrusion L3a and a hollow protrusion L3b are formed, respectively. At a front end portion and a rear end portion of the channel L4, a hollow protrusion L4a and a hollow protrusion L4b are formed, respectively. In an upper face of the upper manifold 52, as shown in FIG. 9, an opening R3a, an opening R5a and an opening R4a are formed in a transversal direction as one set, and sixteen sets of openings (R3a, R5a, R4a) are formed in a longitudinal direction. A channel R3 has the opening R3a as an open end, and the other end communicates with the channel L3; a channel R4 has the opening R4a as an open end, and the other end communicates with the channel L4. A channel R5 has the opening R5a at an upper end and penetrates in a thickness direction of the upper manifold 52, and at the lower end portion, a hollow protrusion R5b is provided.

In the odor blending unit 50 shown in FIG. 7, sixteen sample containers 10 is attached to the recesses 51a, and each sample container 10 is connected to the protrusion R1a or the protrusion R2a through the piping 21, and to the protrusion R5b shown in FIG. 9 through the piping 22. It should be noted that, in the present example, tube made of Teflon (registered trademark) is uses for piping.

As shown in FIG. 10, the solenoid valve 11 has the NC port 11a, the common port 11b and the NO port 11c formed in a row, and the ports 11a, 11b and 11c fit a set of the corresponding openings R3a, R5 and R4a in the upper manifold 52. The electrode 11e is connected to the computer 20 through the drive circuit 20a (see FIG. 11) by wiring (not shown).

Next, the odor blender of the present example will be described. The odor blender shown in FIG. 11 has: two odor blending units 50A, 50B; the computer 20; the drive circuit 20a configured to drive the solenoid valve 11; a measuring unit (sensor part formed of QCM sensor, sensor cell, oscillator, frequency counter and the like; not shown); a suction pump connected to the blend line and the bypass line and configured to drive a gas flow; and a valved flowmeter configured to adjust the flow rate of the blend line and the flow rate of the bypass line.

Each of two odor blending units 50A, 50B has sixteen sample containers 10, and each sample container is connected to the protrusion R1a or R2a through the piping 21, and to the protrusion R5b through the piping 22.

The protrusion L3b of the odor blending unit 50A and the protrusion L3a of the odor blending unit 50B are connected by piping L3c, and two odor blending units 50A,50B communicate with each other as the channel L3. To the protrusion L3b of the odor blending unit 50B, a cap (not shown) is attached, to thereby seal the rear end of the channel L3. On the other hand, the protrusion L3a of the odor blending unit 50A is connected to the above-mentioned sensor cell of the measuring unit through the piping (not shown) and further to the suction pump through the valved flowmeter.

The protrusion L4b of the odor blending unit 50A and the protrusion L4a of the odor blending unit 50B are connected by piping L4c, and two odor blending units 50A, 50B communicate with each other as the channel L4. To the protrusion L4b of the odor blending unit 50B, a cap (not shown) is attached, to thereby seal the rear end of the channel L4. On the other hand, the protrusion L4a of the odor blending unit 50A is connected to the suction pump through the valved flowmeter using piping (not shown).

No piping is connected to the protrusions L1a,L2a, and the channels L1,L2 are opened to the atmosphere.

Next, the operation of the odor blender in the example will be described with reference to FIGS. 7 to 11.

By operating the above-mentioned suction pump to perform suction, gas flows are driven in the blend line and bypass line. First, from the openings of the protrusions L1a,L2a opened to the atmosphere, air is introduced as a carrier gas. The air introduced to the channels L2,L3 is sent to each sample container 10, through the channel R1 or channel R2 and the piping 21. The air sent to the sample container 10, together with the component odor gas in the headspace, flows through the channel R5, and depending on the connection mode of the corresponding solenoid valve 11, is sent to the channel L3 or the channel L4.

Herein, when voltage is not applied to the electrode 11e of the solenoid valve 11, the common port 11b and the NO port 11c are connected, and thus the channel R5 communicates with the channel L4 (bypass line). On the other hand, when voltage is applied to the electrode 11e of the solenoid valve 11, the common port 11b and the NC port 11a are connected, and thus the channel R5 communicates with the channel L3 (blend line).

The solenoid valve 11 is operated based on a control signal output from the computer 20 having a bi-directional digital I/O card (PIO-48D(CB)H, manufactured by Contec Co., Ltd.) installed therein. A switching signal for each solenoid valve 11 generated by the computer 20 is output through the bi-directional digital I/O card and sent to the drive circuit 20a, and in the drive circuit 20a, further to a transistor (2SC1815) through a latch circuit (74ALS575). An application of voltage to the electrode lie of the solenoid valve 11 (3-way solenoid valve LHDS1221211H manufactured by The Lee Co.) is controlled, using a transistor as a switching circuit.

The component odor gas supplied to the channel L3 to which the connection is made by the solenoid valve 11 is, as it flows to the downstream side of the channel L3, mixed (blended) with other component odor gases supplied from other channels R3, and a blended odor is generated. In other words, the channel L3 serves as the blend part.

The blended odor obtained along the channel L3 is sent to the sensor cell of the measuring unit (not shown) connected to the blend line and measured. The measured value obtained by the measuring unit (sensor output vector from the QCM sensor) is transmitted to the computer 20 through a serial line.

The blended odor measured at the measuring unit is discharged from the suction pump through the valved flowmeter. On a discharge side of the suction pump, the activated carbon filter (not shown) is provided, where the component odor gas component is adsorbed by the activated carbon and only air is discharged to the atmosphere.

On the other hand, the component odor gas supplied to the channel L4 (bypass line) through the solenoid valve 11 and the channel R4, together with other component odor gases supplied through the channels R4, flows through the valved flowmeter connected to the bypass line and is discharged from the suction pump. The component odor gas components discharged from the suction pump are adsorbed by the activated carbon filter, and only air is discharged to the atmosphere.

Experiment 1

Next, confirmatory experiment for performance of supplying component odor gas, using the odor blender of the example, will be described.

The conditions for the experiment will be described below.
<Experiment Conditions>
(Time for Switching Solenoid Valve)

The renewal time period (unit time) of the mixing ratio of the component odor gases was set to 1 second, and a connection time for each component odor container was set to 10 ms unit. It should be noted that the response time of the above-mentioned solenoid valve is approximately 1 ms, and relative to 10 ms as the minimum connection time, the solenoid valve operates at sufficiently high speed.
(Odor Blender)

As shown in FIG. 11, two odor blending units each having sixteen sample containers were connected, and thus thirty-two sample containers were attached to the odor blending unit. Among them, one of the sample containers was used as a carrier gas container, and air was used as a carrier gas. For the measurement, a sample container No. 2 which was located closest to the carrier gas container (sample container No. 1) and a sample container No. 32 which was located farthest from the carrier gas container were filled with a component odor (see sample containers No. 1, No. 2, No. 32 in FIG. 11).
(QCM Sensor)

For the QCM sensor, an AT-cut type with 20 MHz was used, and four different types of sensor were prepared, with the sensitive films formed by applying OV-17, TCP, Apiezon L or PEG1000 thereto.
(Component Odor)

As a component odor, 2-hexanone was used, and the sample containers No. 2 and 32 were filled with 2-hexanone. The other sample containers No. 3-31 were left empty.
(Gas Flow Rate)

A flow rate in the blend line and a flow rate in the bypass line were adjusted to 600 mL/min and 3.5 L/min, respectively.
(Supply of Component Odor Gas)

The component odor container which was connected to the blend line within 1 time period (unit time) was set to either No. 2 or No. 32, and a concentration of the component odor gas of the odor, blended when a duty cycle (which is a rate of the connection time within 1 time period) is 100%, was set to 100% (which is equal to the gas concentration in the head-space), and response of the QCM sensor was measured while changing the duty cycle, such as 10, 20, 30, 40, 50%.

Next, with reference to FIGS. 12 and 13, experimental results showing the performance of supplying the component odor gas by the odor blender according to the example will be described.

Figure 12:
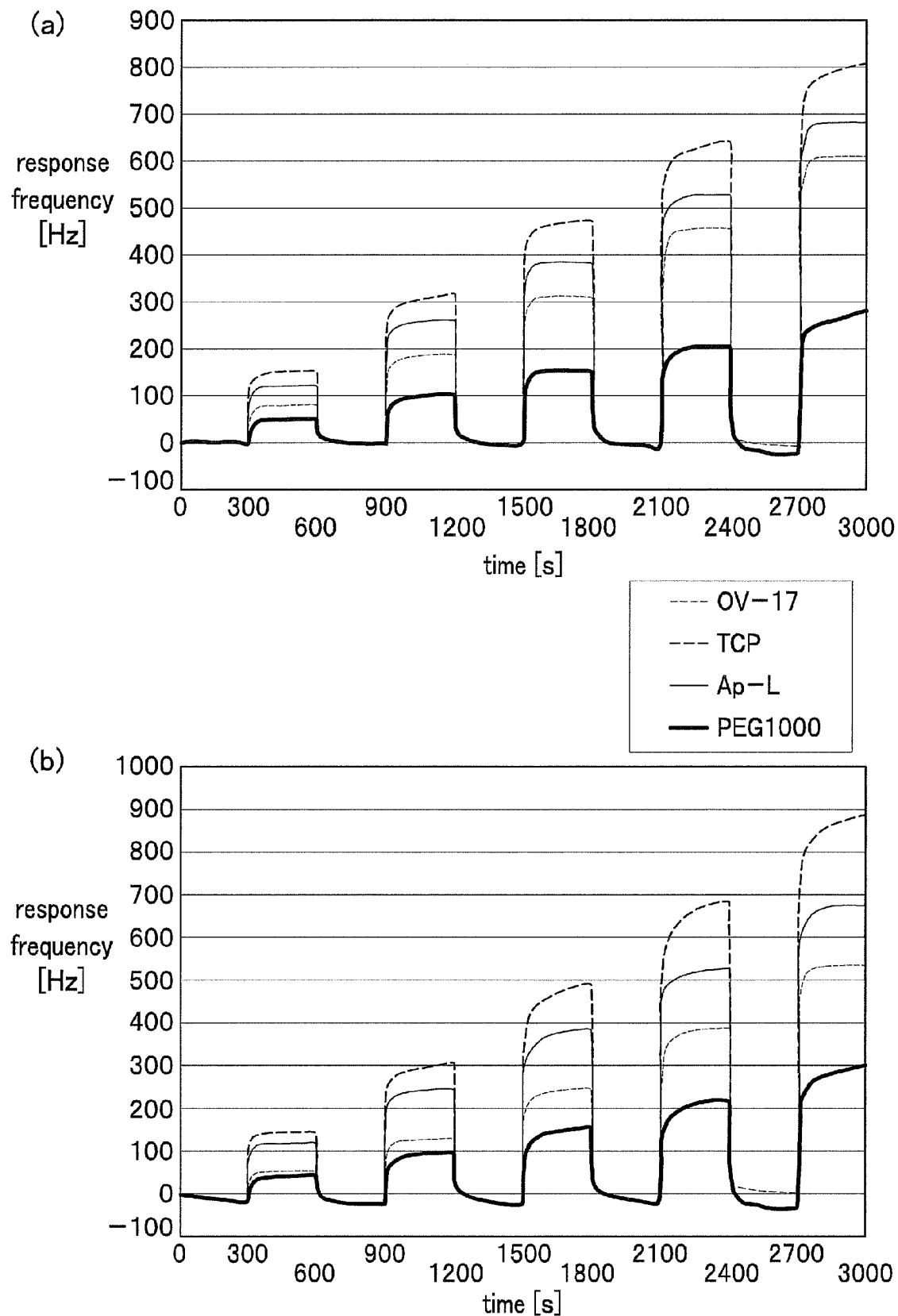
FIG. 12 shows graphs indicating changes in sensor output when various concentrations of component odor gas are supplied by odor blender according to one embodiment, in which (a) is measurement results when the component odor gas is supplied from a component No. 2, and (b) is measurement results when the component odor gas is supplied from a component No. 32.
Figure 15:
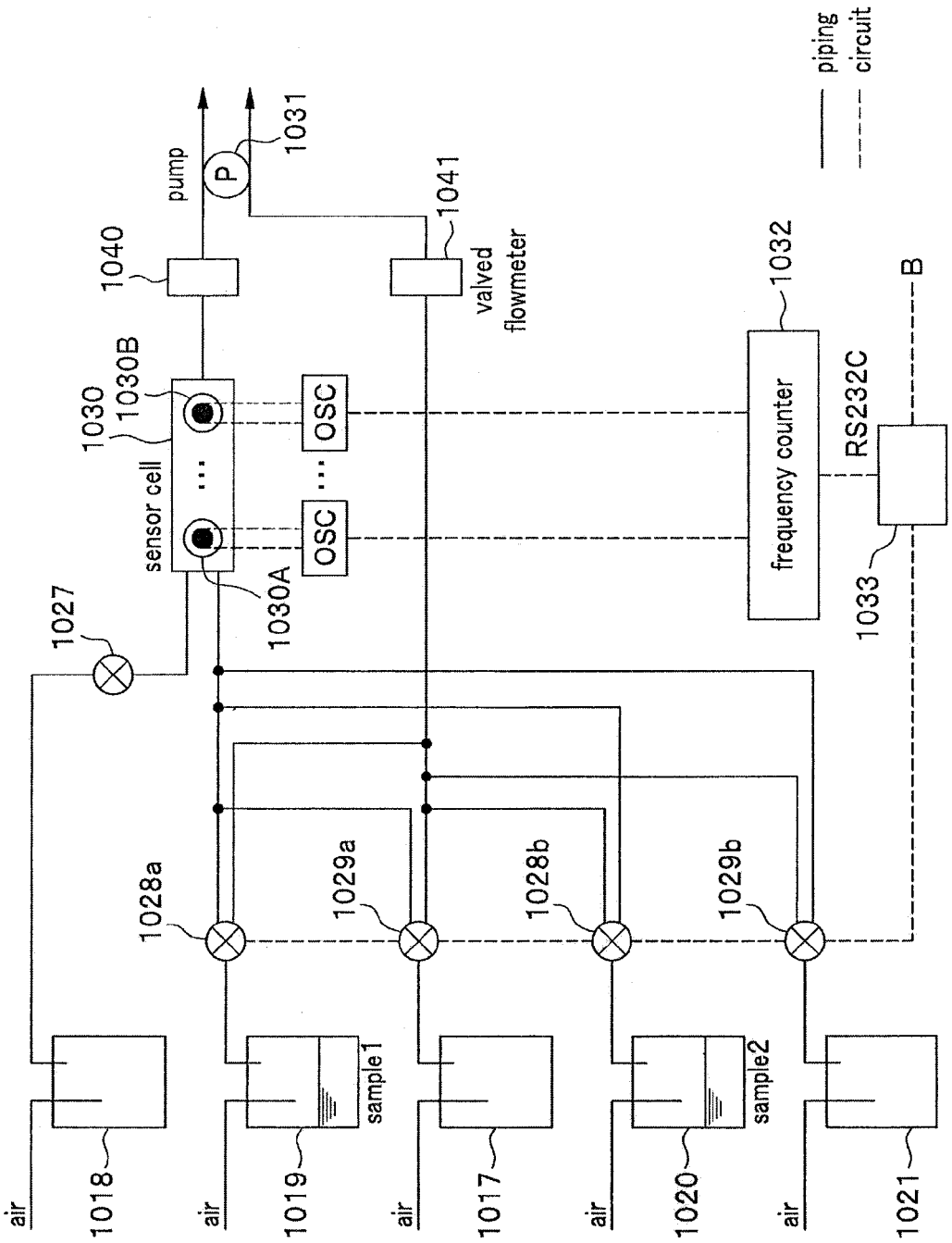
FIG. 15 is a diagram showing a structure of a conventional odor blender.
Figure 16:
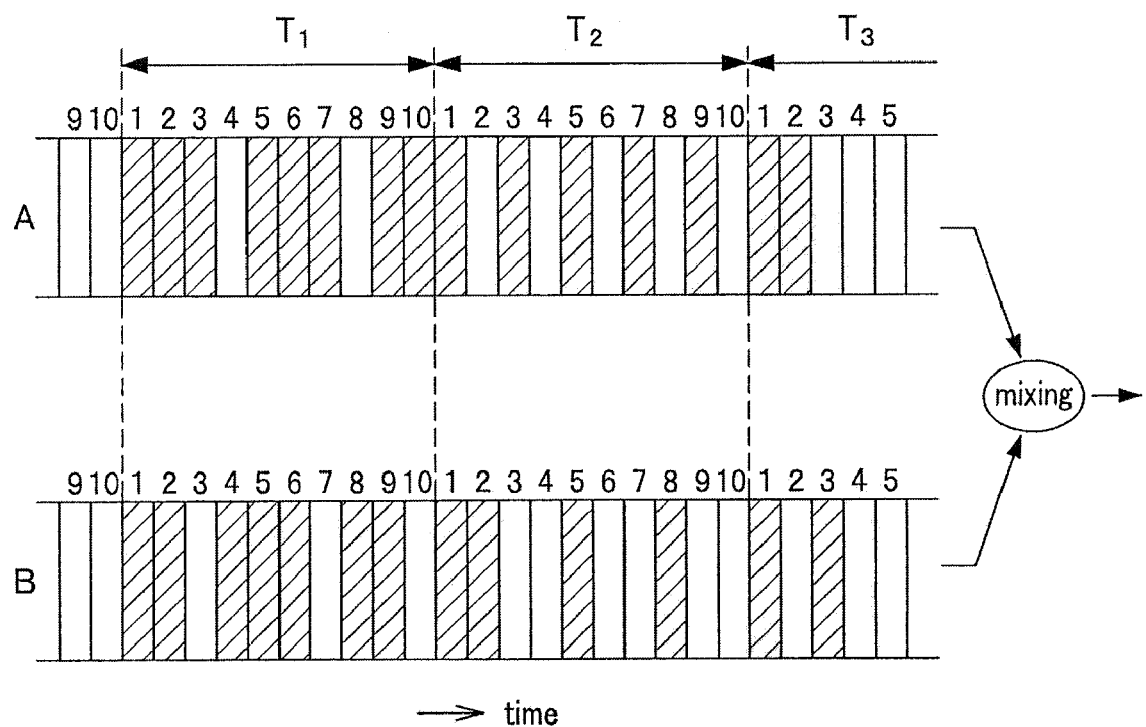
FIG. 16 is a diagram illustrating modes of supplying component odor gas in a conventional odor blender.

Herein, FIG. 12 show graphs indicating measurement result of a relation between gas concentration of the component odor gas supplied from the component odor container and response of the QCM sensor, in which (a) is measurement results when the component odor gas is supplied from component odor container No. 2, and (b) is measurement results when the component odor gas is supplied from component odor container No. 32. FIG. 13 shows graphs indicating relationships between concentration of the component odor gas from the component odor container and a sensor output, in which (a) is a relationship between the gas concentration and the sensor output when a component odor gas is supplied from a component odor container No. 2, and (b) is a relationship between the gas concentration and the sensor output when a component odor gas is supplied from a component odor container No. 32.

FIG. 12(a) is a graph showing outputs (response frequency) of the four types of the QCM sensor, when 2-hexanone as component odor gas is supplied from the component odor container No. 2. In the graph, a horizontal axis indicates time. During a time period of 300-600 second, a time period of 900-1200 second, a time period of 1500-1800 second, a time period of 2100-2400 second, and a time period of 2700-3000 second, 2-hexanone was supplied with the duty cycle for the solenoid valve to connect with the blend line of 10%, 20%, 30%, 40% and 50%, respectively. During a time period of 0-300 second, a time period of 600-900 second, a time period of 1200-1500 second, a time period of 1800-2100 second and a time period of 2400-2700 second, only the carrier gas was supplied.

Depending on the types of the sensitive film, response frequency varies, but it is apparent that all response frequency of the QCM sensor increased, in accordance with the supply amount (duty cycle) of the component odor gas.

Based on the experimental results shown in FIG. 12(a), a relationship between the duty cycle for supplying the component odor gas and the response frequency of the QCM sensor was obtained, which is shown in FIG. 13(a).

It is clear that the response frequency for each QCM sensor is nearly proportional to the duty cycle.

It is known that the QCM sensor used in the present experiment responds almost linearly to the gas concentration of 2-hexanone. Therefore, it was found that the duty cycle and the gas concentration supplied to the QCM sensor are nearly proportional. In other words, it is confirmed that the supply of the component odor gas to the blend line can be controlled, in proportion to the duty cycle.

FIG. 12(b) is a graph showing outputs (response frequency) of the four types of the QCM sensor, when 2-hexanone as component odor gas was supplied from the sample container No. 32, instead of the sample container No. 2. The measurement conditions are the same as those using the sample container No. 2, and thus a duplicate description is omitted.

Like the description regarding the sample container No. 2, based on the experimental results shown in FIG. 12(b), a relationship between the duty cycle for supplying the component odor gas and the response frequency of the QCM sensor was obtained. The results are shown in FIG. 13(b).

this value, the concentration was expressed. The preset concentration profile in the case where the number of the component odors (number of the component odor containers) is 4 (M=4) is shown in FIG. 14(a), and the concentration yi(t) calculated in the case where the solenoid valve is in an ON mode (state in which the component odor container is connected to the blend line) is shown in FIG. 14(b). In this case, n is set to 100. During the first 1 second, a correct yi(t) was not obtained, but this is because at least 100 data are necessary for obtaining a moving average, and it is clear that after 1 second, the control of the opening and the closing of solenoid valve follows the preset concentration. In the results shown in FIG. 14(b), there is observed some noise, but in practice, this level of noise does not cause problems.

Next, in the following Table 1, the solenoid valve which became turned on between 2000 ms and 2220 ms in FIG. 14(b), i.e., the component odor container number connected to the blend line, is shown in time-series. As is apparent from the results shown in Table 1, it was elucidated that, by switching the component odor containers to be connected to the blend line per unit time (10 ms), more homogeneous odor blending can be attained as compared with a common PWM.

TABLE 1

| time t[ms] | 2000 | 2010 | 2020 | 2030 | 2040 | 2050 | 2060 | 2070 |
|---|---|---|---|---|---|---|---|---|
| component odor (turned on) | 1 | 3 | 2 | 1 | 2 | 3 | 4 | 3 |
| time t[ms] | 2080 | 2090 | 2100 | 2110 | 2120 | 2130 | 2140 | 2150 |
| component odor (turned on) | 4 | 2 | 1 | 4 | 2 | 5 | 1 | 1 |
| time t[ms] | 2160 | 2170 | 2180 | 2190 | 2200 | 2210 | 2220 | |
| component odor (turned on) | 4 | 1 | 1 | 1 | 2 | 1 | 1 | |

As in the case where the sample container No. 2 is used, the duty cycle for supplying the component odor gas and the response frequency of the QCM sensor are nearly proportional, and also in the case where the sample container No. 32 is used, it was found that the duty cycle and the gas concentration supplied to the QCM sensor are nearly proportional. In other words, it is confirmed that the supply of the component odor gas to the blend line can be controlled, in proportion to the duty cycle.

Further, response property of each of the QCM sensors shown in FIG. 13(a) and response property of each of the QCM sensor shown in FIG. 13(b) are nearly equal, and it is confirmed that the positional difference of the sample container hardly results in the difference in supply.

As described above, with the use of the odor blender according to the present invention, it is confirmed that the component odor gas can be appropriately supplied for the purpose of generating the blended odor.

Example 2

In order to check the action of the odor blender of the sixth embodiment, a simulation was performed using a numerical analysis software (MATLAB manufactured by Cybernet Systems Co., Ltd.). The unit time was set to 10 ms, and the concentration when the component odor of interest is turned on all the time (i.e., the component odor container of interest is connected to the blend line) was set to 100%, and relative to

The invention claimed is:

1. An odor blender comprising:
N component odor containers each configured to supply a component odor gas, wherein N is an integer of 2 or more,
M carrier gas containers each configured to supply a carrier gas, wherein M is an integer of 1 or more and less than N,
a blend part configured to blend the component odor gases,
a blend line configured to lead the component odor gases from the N component odor containers to the blend part,
a bypass line configured to discharge the component odor gases from the N component odor containers without passing through the blend part,
N+M solenoid valves each of which is a three-way valve configured to have one of the N component odor containers and the M carrier gas containers communicate with any one of the blend line and the bypass line, and
a control unit configured to control the switching of the connections by the N+M solenoid valves,
wherein the control unit sets the number of the component odor containers connected to the blend line at the same time to M or less but not less than one out of the N component odor containers; connects the same number of the carrier gas containers to the bypass line as the number of the component odor containers connected to the blend line, and controls a time frame for the connection from the component odor container to the blend line per predetermined time period, based on a predetermined component odor gas mixing ratio.

2. The odor blender according to claim 1, wherein the component odor gas is supplied from a headspace of the corresponding component odor container.

3. The odor blender according to claim 1, wherein each of the blend line and the bypass line has a flow regulating unit configured to adjust a corresponding flow rate.

4. An odor recorder comprising:
an odor blender comprising:
N component odor containers each configured to supply a component odor gas, wherein N is an integer of 2 or more,
M carrier gas containers each configured to supply a carrier gas, wherein M is an integer of 1 or more and less than N,
a blend part configured to blend the component odor gases,
a blend line configured to lead the component odor gases from the N component odor containers to the blend part,
a bypass line configured to discharge the component odor gases from the N component odor containers without passing through the blend part,
N+M solenoid valves each of which is a three-way valve configured to have one of the N component odor containers and the M carrier gas containers communicate with any one of the blend line and the bypass line, and
a control unit configured to control the switching of the connections by the N+M solenoid valves,
wherein the control unit sets the number of the component odor containers connected to the blend line at the same time to M or less but not less than one out of the N component odor containers; connects the same number of the carrier gas containers to the bypass line as the number of the component odor containers connected to the blend line; and controls a time frame for the connection from the component odor container to the blend line per predetermined time period, based on a predetermined component odor gas mixing ratio,
a measuring unit configured to measure odor disposed on the blend line,
wherein the control unit determines the mixing ratio of component odor gases based on a target value determined in advance and a measured value of an odor blended in the blend part measured by the measuring unit.

5. An odor reproducer comprising:
an odor blender comprising:
N component odor containers each configured to supply a component odor gas, wherein N is an integer of 2 or more,
M carrier gas containers each configured to supply a carrier gas, wherein M is an integer of 1 or more and less than N,
a blend part configured to blend the component odor gases,
a blend line configured to lead the component odor gases from the N component odor containers to the blend part,
a bypass line configured to discharge the component odor gases from the N component odor containers without passing through the blend part,
N+M solenoid valves each of which is a three-way valve configured to have one of the N component odor containers and the M carrier gas containers communicate with any one of the blend line and the bypass line, and
a control unit configured to control the switching of the connections by the N+M solenoid valves,
wherein the control unit sets the number of the component odor containers connected to the blend line at the same time to M or less but not less than one out of the N component odor containers; connects the same number of the carrier gas containers to the bypass line as the number of the component odor containers connected to the blend line; and controls a time frame for the connection from the component odor container to the blend line per predetermined time period, based on a predetermined component odor gas mixing ratio,
wherein a gas flow of each of the blend line and the bypass line is driven by a gas flow driving unit disposed on an upstream end of the gas flow.

6. An odor recording and reproducing system comprising:
odor blenders, each of the odor blenders comprising:
N component odor containers each configured to supply a component odor gas, wherein N is an integer that is equal to or more than 2,
M carrier gas containers each configured to supply a carrier gas, wherein M is an integer that is equal to or more than 1 and less than N,
a blend part configured to blend the component odor gases,
a blend line configured to lead the component odor gases from the N component odor containers to the blend part,
a bypass line configured to discharge the component odor gases from the N component odor containers without passing through the blend part,
N+M solenoid valves each of which is a three-way valve configured to have one of the N component odor containers and the M carrier gas containers communicate with any one of the blend line and the bypass line, and
a control unit configured to control the switching of the connections by the N+M solenoid valves,
wherein the control unit sets the number of the component odor containers connected to the blend line at the same time to M or less but not less than one out of the N component odor containers; connects the same number of the carrier gas containers to the bypass line as the number of the component odor containers connected to the blend line; and controls a time frame for the connection from the component odor container to the blend line per predetermined time period, based on a predetermined component odor gas mixing ratio,
at least one odor recorder connected to a network, the odor recorder comprising one of the odor blenders, and a measuring unit configured to measure odor disposed on the blend line, wherein the control unit determines the mixing ratio of component odor gases based on a target value determined in advance and a measured value of an odor blended in the blend part measured by the measuring unit;
at least one odor reproducer connected to the network, the odor reproducer comprising the other odor blender, wherein a gas flow of each of the blend line and the bypass line is driven by a gas flowing driving unit disposed on an upstream end of the gas flow, and
a management computer which is connected to the network,
wherein the management computer obtains through the network the mixing ratio determined by the odor recorder, and the management computer sends the obtained mixing ratio to the odor reproducer through the network and controls the odor reproducer to blend the component odor gases based on the obtained mixing ratio.

7. An odor blender comprising:

N component odor containers each configured to supply a component odor gas, wherein N is an integer of 2 or more, M carrier gas containers each configured to supply a carrier gas, wherein M is an integer of 1 or more and less than N, a blend part configured to blend the component odor gases, a blend line configured to lead the component odor gases from the N component odor containers to the blend part, a bypass line configured to discharge the component odor gases from the N component odor containers without passing through the blend part, N+M solenoid valves each of which is a three-way valve configured to have one of the N component odor containers and the M carrier gas containers communicate with any one of the blend line and the bypass line, and a control unit configured to control the switching of the connections by the N+M solenoid valves, wherein, when xi(t) represents a preset concentration of a component odor at the present moment t, and yi(t) represents an average concentration for past time periods nτ wherein n is a positive integer, the control unit selects, every predetermined unit time τ, a single component odor container that supplies a component odor gas with which xi(t) becomes larger than yi(t−1) and a relative error of both becomes the maximum, and connects the selected component odor container to the blend line.

8. The odor blender according to claim 7, wherein, when xi(t) represents the preset concentration of the component odor i at the present moment t, and yi(t) represents a ratio of the connection of the component odor i to the blend line during the past time periods nτ from the moment t wherein n is a positive integer, the control unit selects, every predetermined unit time τ, a single component odor container that supplies a component odor gas with which xi(t) becomes larger than yi(t−1) and the relative error ((xi(t)−yi(t−1))/xi(t)) becomes the maximum, and connects the selected component odor container to the blend line.

9. The odor blender according to claim 7, wherein, when there is no corresponding component odor, solely a carrier gas container is connected to the blend line at the moment t.

10. The odor blender according to claim 7, wherein each of the blend line and the bypass line has a flow regulating unit configured to adjust a corresponding flow rate.

11. An odor recorder comprising:

an odor blender comprising:

N component odor containers each configured to supply a component odor gas, wherein N is an integer of 2 or more, M carrier gas containers each configured to supply a carrier gas, wherein M is an integer of 1 or more and less than N, a blend part configured to blend the component odor gases, a blend line configured to lead the component odor gases from the N component odor containers to the blend part, a bypass line configured to discharge the component odor gases from the N component odor containers without passing through the blend part, N+M solenoid valves each of which is a three-way valve configured to have one of the N component odor containers and the M carrier gas containers communicate with any one of the blend line and the bypass line, and a control unit configured to control the switching of the connections by the N+M solenoid valves, wherein, when xi(t) represents a preset concentration of a component odor i at the present moment t, and yi(t) represents an average concentration for past time periods nτ wherein n is a positive integer, the control unit selects, every predetermined unit time τ, a single component odor container that supplies a component odor gas with which xi(t) becomes larger than yi(t−1) and a relative error of both becomes the maximum, and connects the selected component odor container to the blend line; and a measuring unit configured to measure odor disposed on the blend line, wherein the control unit determines the mixing ratio of component odor gases based on a target value determined in advance and a measured value of an odor blended in the blend part measured by the measuring unit.

12. An odor reproducer comprising:

an odor blender comprising:

N component odor containers each configured to supply a component odor gas, wherein N is an integer of 2 or more, M carrier gas containers each configured to supply a carrier gas, wherein M is an integer of 1 or more and less than N, a blend part configured to blend the component odor gases, a blend line configured to lead the component odor gases from the N component odor containers to the blend part, a bypass line configured to discharge the component odor gases from the N component odor containers without passing through the blend part, N+M solenoid valves each of which is a three-way valve configured to have one of the N component odor containers and the M carrier gas containers communicate with any one of the blend line and the bypass line, and a control unit configured to control the switching of the connections by the N+M solenoid valves, wherein, when xi(t) represents a preset concentration of a component odor i at the present moment t, and yi(t) represents an average concentration for past time periods nτ wherein n is a positive integer, the control unit selects, every predetermined unit time τ, a single component odor container that supplies a component odor gas with which xi(t) becomes larger than yi(t−1) and a relative error of both becomes the maximum, and connects the selected component odor container to the blend line, wherein a gas flow of each of the blend line and the bypass line is driven by a gas flow driving unit disposed on an upstream end of the gas flow.

13. An odor recording and reproducing system comprising:

odor blenders, each of the odor blenders comprising:

N component odor containers each configured to supply a component odor gas, wherein N is an integer that is equal to or more than 2, M carrier gas containers each configured to supply a carrier gas, wherein M is an integer that is equal to or more than 1 and less than N, a blend part configured to blend the component odor gases, a blend line configured to lead the component odor gases from the N component odor containers to the blend part, a bypass line configured to discharge the component odor gases from the N component odor containers without passing through the blend part, N+M solenoid valves each of which is a three-way valve configured to have one of the N component odor containers and the M carrier gas containers communicate with any one of the blend line and the bypass line, and a control unit configured to control the switching of the connections by the N+M solenoid valves, wherein, when $x_i(t)$ represents a preset concentration of a component odor i at the present moment t, and $y_i(t)$ represents an average concentration for past time periods $n\tau$ wherein n is a positive integer, the control unit selects, every predetermined unit time $\tau$, a single component odor container that supplies a component odor gas with which $x_i(t)$ becomes larger than $y_i(t-1)$ and a relative error of both becomes the maximum, and connects the selected component odor container to the blend line, at least one odor recorder connected to a network, the odor recorder comprising one of the odor blenders, and a measuring unit configured to measure odor disposed on the blend line, wherein the control unit determines the mixing ratio of component odor gases based on a target value determined in advance and a measured value of an odor blended in the blend part measured by the measuring unit, at least one odor reproducer connected to the network, the odor reproducer comprising the other odor blender, wherein a gas flow of each of the blend line and the bypass line is driven by a gas flow driving unit disposed on an upstream end of the gas flow, and a management computer which is connected to the network, wherein the management computer obtains through the network the mixing ratio determined by the odor recorder, and the management computer sends the obtained mixing ratio to the odor reproducer through the network and controls the odor reproducer to blend the component odor gases based on the obtained mixing ratio.

* * * * *